US008524477B2

(12) United States Patent
Opstelten

(10) Patent No.: US 8,524,477 B2
(45) Date of Patent: *Sep. 3, 2013

(54) METHODS TO OBTAIN RECOMBINANT PROTEINS WITH INCREASED SIALYLATION FROM CELLS THAT EXPRESS ADENOVIRUS E1A PROTEIN, AND PROTEINS OBTAINED THEREBY

(75) Inventor: Dirk J. E. Opstelten, Oegstgeest (NL)

(73) Assignee: Crucell Holland B.V., Leiden (NL)

( * ) Notice: Subject to any disclaimer, the term of this patent is extended or adjusted under 35 U.S.C. 154(b) by 895 days.

This patent is subject to a terminal disclaimer.

(21) Appl. No.: 12/592,384

(22) Filed: Nov. 23, 2009

(65) Prior Publication Data
US 2010/0221774 A1     Sep. 2, 2010

Related U.S. Application Data

(60) Division of application No. 11/793,998, filed as application No. PCT/EP2005/057205 on Dec. 28, 2005, now Pat. No. 7,642,078, application No. 12/592,384, which is a continuation-in-part of application No. 11/026,518, filed on Dec. 30, 2004, and a continuation-in-part of application No. 10/497,832, filed as application No. PCT/NL02/00804 on Dec. 9, 2002, now Pat. No. 7,504,248, said application No. 11/793,998 is a continuation-in-part of application No. 11/102,073, filed on Apr. 8, 2005, now Pat. No. 7,297,680, which is a continuation-in-part of application No. 11/026,518, filed on Dec. 30, 2004, and a continuation-in-part of application No. 10/494,140, filed as application No. PCT/NL02/00686 on Oct. 29, 2002, now Pat. No. 7,304,031.

(51) Int. Cl.
*C12N 9/04* (2006.01)

(52) U.S. Cl.
USPC .......................................................... 435/190

(58) Field of Classification Search
None
See application file for complete search history.

(56) References Cited

U.S. PATENT DOCUMENTS

| | | | |
|---|---|---|---|
| 5,494,790 A | 2/1996 | Sasaki et al. | |
| 5,789,247 A | 8/1998 | Ballay et al. | |
| 5,856,298 A | 1/1999 | Strickland | |
| 6,855,544 B1 * | 2/2005 | Hateboer et al. | 435/325 |
| 7,297,680 B2 | 11/2007 | Opstelten et al. | |
| 2005/0164917 A1 | 7/2005 | Opstelten et al. | |

FOREIGN PATENT DOCUMENTS

| | | |
|---|---|---|
| EP | 1 533 380 | 5/2005 |
| WO | WO 00/63403 | 10/2000 |
| WO | WO 03/038100 | 5/2003 |
| WO | WO 03/048197 | 6/2003 |

OTHER PUBLICATIONS

Zhang et al., Stable expression of human alpha-2,6-sialyltransferase in Chinese hamster ovary cells: functional consequences for human erythropoietin expression and bioactivity, Biochimica et Biophysica Acta, 1998, pp. 441-452, vol. 1425.
PCT International Search Report, PCT/EP2005/057205, dated Apr. 11, 2006.
PCT International Preliminary Report on Patentability, PCT/EP2005/057205, dated Dec. 20, 2006.
Office Action for U.S. Appl. No. 11/793,998, dated Apr. 9, 2008.
Office Action for U.S. Appl. No. 11/793,998, dated Feb. 2, 2009.
Notice of Allowance for U.S. Appl. No. 11/793,998, dated Sep. 2, 2009.
U.S. Appl. No. 11/657,202, filed Jan. 24, 2007, Opstelten et al., Methods and Means for Producing Proteins With Predetermined Post-Translational Modifications.
U.S. Appl. No. 11/888,776, filed Aug. 1, 2007, Opstelten et al., Methods and Means for Producing Proteins With Predetermined Post-Translational Modifications.
U.S. Appl. No. 11/026,518, filed Dec. 30, 2004, Uytdehaag et al., Overexpression of Enzymes Involved in Post-Translational Protein Modifications in Human Cells.
U.S. Appl. No. 11/731,246, filed Mar. 30, 2007, Uytdehaag et al., Overexpression of Enzymes Involved in Post-Translational Protein Modifications in Human Cells.
U.S. Appl. No. 11/879,422, filed Jul. 16, 2007, Marzio et al., Production of Viruses, Viral Isolates and Vaccines.
U.S. Appl. No. 11/070,890, filed Mar. 2, 2005, Bout et al., Recombinant Protein Production in Permanent Amniocytic Cells That Comprise Nucleic Acid Encoding Adenovirus E1A and E1B Proteins.
U.S. Appl. No. 11/821,107, filed Jun. 20, 2007, Opstelten et al., Compositions of Erythropoietin Isoforms Comprising Lewis-X Structures and High Sialic Acid Content.
U.S. Appl. No. 11/793,998, filed Jun. 21, 2007, Dirk J. E. Opstelten, Methods to Obtain Recombinant Proteins With Increased Sialylation From Cells That Express Adenovirus E1A Protein, and Proteins Obtained Thereby.

* cited by examiner

*Primary Examiner* — Suzanne M Noakes
(74) *Attorney, Agent, or Firm* — TraskBritt

(57) ABSTRACT

Provided are compositions comprising one or more isoforms of an erythropoietin ("EPO") comprising glycans linked thereto, wherein the glycans have Lewis x structures and on average at least six sialic acid moieties per EPO molecule. Further provided are methods for obtaining a composition comprising one or more isoforms of EPO comprising glycans linked thereto, wherein the glycans comprise on average at least six sialic acids per EPO molecule and from zero to two Lewis x structures, the method comprising: a) providing a eukaryotic cell containing a nucleic acid sequence encoding an adenoviral E1A protein in expressible format and a nucleic acid encoding EPO in expressible format, wherein the cell further contains a nucleic acid sequence encoding a sialyltransferase, e.g., an α-2,6-sialyltransferase or an α-2,3-sialyltransferase, under control of a heterologous promoter; b) culturing the cell in a serum-free culture medium and allowing expression of EPO in the cell; c) harvesting the expressed EPO from the cell and/or from the culture medium; and d) purifying and fractionating the EPO to obtain fractions that have an increased average sialic acid content of the N-linked glycans per EPO molecule, to obtain a composition comprising one or more isoforms of an EPO comprising glycans linked thereto, wherein the glycans comprise on average at least six sialic acids per EPO molecule and from zero to two Lewis x structures.

20 Claims, 13 Drawing Sheets

A = Eprex
B = PER.C6-α2,6ST-EPO
C = PER.C6-EPO

PER.C6-EPO

* Number of sialic acids per glycan

PER.C6-ST-EPO

* Number of sialic acids per glycan

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial
<220> FEATURE:
<223> OTHER INFORMATION: forward EPO primer

<400> SEQUENCE: 1
ccaggcgcgc caccatgggg gtgcacgaat gtcc                               34

<210> SEQ ID NO 2
<211> LENGTH: 30
<212> TYPE: DNA
<213> ORGANISM: Artificial
<220> FEATURE:
<223> OTHER INFORMATION: reverse EPO primer

<400> SEQUENCE: 2
ccgggttaac tcatctgtcc cctgtcctgc                                    30

<210> SEQ ID NO 3
<211> LENGTH: 23
<212> TYPE: DNA
<213> ORGANISM: Artificial
<220> FEATURE:
<223> OTHER INFORMATION: forward alfa-2,3-sialyltransferase primer

<400> SEQUENCE: 3
ggactagtgg atccgccacc atg                                           23

<210> SEQ ID NO 4
<211> LENGTH: 30
<212> TYPE: DNA
<213> ORGANISM: Artificial
<220> FEATURE:
<223> OTHER INFORMATION: reverse alfa-2,3-sialyltransferase primer

<400> SEQUENCE: 4
gctctagatc agaaggacgt gaggttcttg                                    30
```

METHODS TO OBTAIN RECOMBINANT PROTEINS WITH INCREASED SIALYLATION FROM CELLS THAT EXPRESS ADENOVIRUS E1A PROTEIN, AND PROTEINS OBTAINED THEREBY

CROSS-REFERENCE TO RELATED APPLICATIONS

This application a divisional of U.S. patent application Ser. No. 11/793,998 filed Jun. 21, 2007, now U.S. Pat. No. 7,642, 078, which is a national phase of PCT/EP2005/057205, filed Dec. 28, 2005, designating the United States, and published in English on Jul. 6, 2006, as WO 2006/070011 A1. This application and U.S. Ser. No. 11/793,998 are continuations-in-part of U.S. Ser. No. 11/026,518 filed Dec. 30, 2004, pending, and are also continuations-in-part of U.S. patent application Ser. No. 11/102,073 filed Apr. 8, 2005, now U.S. Pat. No. 7,297,680 (Nov. 20, 2007). This application and U.S. patent application Ser. No. 11/793,998 both claim the benefit, under 35 U.S.C. §120 and the Paris Convention, to both U.S. patent application Ser. No. 11/026,518 filed Dec. 30, 2004 and U.S. patent application Ser. No. 11/102,073 filed Apr. 8, 2005, now U.S. Pat. No. 7,297,680. U.S. patent application Ser. No. 11/102,073 is also a continuation-in-part of U.S. patent application Ser. No. 11/026,518. U.S. patent application Ser. No. 11/102,073 is further a continuation-in-part of U.S. patent application Ser. No. 10/494,140, filed Apr. 29, 2004, now U.S. Pat. No. 7,304,031 (Dec. 4, 2007), which published on Jul. 28, 2005, which was a national phase entry under 35 U.S.C. §371 of PCT International Application No. PCT/NL02/00686, filed on Oct. 29, 2002, published in English as PCT International Patent Publn. WO 03/038100 A1 on May 8, 2003. U.S. patent application Ser. No. 11/026, 518 is a continuation-in-part of U.S. patent application Ser. No. 10/497,832, filed Jan. 10, 2005, now U.S. Pat. No. 7,504, 248, which was the national phase entry under 35 U.S.C. §371 of PCT International Application Number PCT/NL02/00804, filed on Dec. 9, 2002, published in English as PCT International Patent Publication WO 03/048348 A2 on Jun. 12, 2003. The contents of the entirety of the patents and patent applications cited in this patent application are incorporated herein by this reference.

TECHNICAL FIELD

The invention relates to the field of biotechnology and recombinant protein production, in particular to the glycosylation of recombinant proteins such as erythropoietin, more in particular to glycosylation of recombinant proteins when produced in adenovirus E1A-expressing cells.

BACKGROUND

As shown in WO 00/63403, immortalized human embryonic retina cells expressing at least an adenovirus E1A protein can be suitably used for the production of recombinant proteins.

Recombinant proteins having N-linked glycosylation produced in cells that express adenovirus E1A have a specific glycosylation profile, for instance, characterized by the presence of Lewis x structures, as described in WO 03/038100.

Another characteristic of the proteins produced thus far in E1A-expressing cells appeared as relatively low galactosylation and low sialylation of the N-linked glycans (WO 03/038100). For certain purposes, this may be an advantage; but for other purposes, higher levels of galactosylation and, preferably, also sialylation, may be beneficial.

For instance, erythropoietin (EPO) that is produced in cells expressing E1A has a pronounced number of Lewis x structures and a relatively low percentage of galactosylation and sialylation in the N-linked glycans (WO 03/038100), resulting in molecules that are very suitable for treatment of ischemia/reperfusion injuries, but may be less suitable for the treatment of anemia. For the treatment of anemia, it has been established that a high degree of sialylation of EPO is beneficial to increase the half-life of the EPO in serum of treated subjects, and thereby the time when the substance is active in increasing the red blood cell count (Goldwasser et al., 1974).

Hence, for the treatment of ischemia/reperfusion injuries, the expression of EPO in E1A-expressing cells has the potential advantage of a preferred glycosylation pattern of the produced EPO for this use. However, for other uses of EPO, different glycosylation patterns may be beneficial.

For other proteins, similar situations may exist; i.e., for certain uses, the specific glycosylation pattern observed upon expression in E1A-expressing cells may be highly beneficial, while for other purposes, a different glycosylation profile may be more suitable.

Over-expression of a sialyltransferase in a cell to increase sialylation of recombinant proteins produced in that cell has been described for other cell types (e.g., Grabenhorst et al., 1995; Minch et al., 1995; Jenkins et al., 1998; Zhang et al., 1998; Weikert et al., 1999; Fukuta et al., 2000; Prati et al., 2000). It was, however, unknown before whether this approach could also lead to desired results in E1A-expressing cells, given the complexities of glycosylation and the still unclear role of E1A therein (WO 03/038100). In particular, the interplay and potential competition between the various glycosyltransferases and other factors in the glycosylation process in cells that express E1A rendered the outcome of over-expression of a sialyltransferase in such cells unforeseen and unpredictable in terms of glycosylation patterns of proteins thus produced.

SUMMARY OF THE INVENTION

For the purpose of broadening the potential use spectrum of recombinant proteins produced in E1A-expressing cells, it could be beneficial to increase the galactosylation and sialylation of such proteins. Provided are methods to accomplish this. Further provided are novel erythropoietin compositions obtainable from E1A-expressing cells.

Provided further are methods of decreasing the average content of LacdiNAc structures on proteins recombinantly expressed in a cell, for instance, a cell expressing E1A of an adenovirus.

Provided are compositions comprising one or more isoforms of an erythropoietin- (EPO-) comprising glycans linked thereto, characterized in that the glycans comprise, on average: a) at least 0.5, preferably at least one, Lewis x structure per. EPO molecule, and b) at least six sialic acid moieties per EPO molecule. Preferably, the glycans comprise, on average, at least seven, more preferably at least eight, still more preferably at least nine, even more preferably at least ten, even still more preferably at least eleven sialic acid moieties per EPO molecule. In certain embodiments, the glycans comprise, on average: a) between one and two Lewis x structures per EPO molecule, and b) between eight and ten sialic acid moieties per EPO molecule. In other embodiments, the glycans comprise, on average: a) between 0.5 and one Lewis x structure per EPO molecule, and b) between 11 and 13 sialic acid moieties per EPO molecule. In certain embodiments, an EPO is human EPO having three N-linked glycans.

Further provided are methods for obtaining a composition comprising one or more isoforms of an erythropoietin- (EPO-) comprising glycans linked thereto, wherein the glycans comprise, on average, at least six sialic acids per EPO molecule and from zero to two Lewis x structures, the method comprising: a) providing a eukaryotic cell containing a nucleic acid sequence encoding an adenoviral E1A protein in expressible format and further containing a nucleic acid encoding an EPO in expressible format, wherein the cell further contains a nucleic acid sequence encoding a sialyltransferase, preferably an α-2,6-sialyltransferase or an α-2,3-sialyltransferase, under control of a heterologous promoter; b) culturing the cell in a serum-free culture medium and allow expression of an EPO in the cell; c) harvesting the expressed EPO from the cell and/or from the culture medium; and d) purifying and fractionating the EPO to obtain fractions that have an increased average sialic acid content of the N-linked glycans per EPO molecule, to obtain a composition comprising one or more isoforms of an EPO-comprising glycans linked thereto wherein the glycans comprise, on average, at least six sialic acids per EPO molecule and from zero to two Lewis x structures.

In certain embodiments, the eukaryotic cell containing a nucleic acid sequence encoding an adenoviral E1A protein in expressible format is derived from a human embryonic retina cell, preferably from a PER.C6™ cell such as deposited on Feb. 29, 1996, at the ECACC under no. 96022940, with the ECACC, CAMR, Salisbury, Wiltshire, SP4 OJG, United Kingdom. In certain embodiments, the glycans comprise, on average, less than one Lewis x structure and at least ten sialic acids per EPO molecule. In further embodiments, the glycans comprise, on average, less than one Lewis x structure, preferably no detectable Lewis x structure, and between 10 and 15 sialic acids per EPO molecule. In other embodiments, the glycans comprise, on average, less than 0.3 Lewis x structure, preferably no detectable Lewis x structure, and between 13 and 15 sialic acids per EPO molecule. In certain embodiments, the composition comprises four or less EPO isoforms together accounting for at least 70% of the EPO present in the composition.

It will be appreciated by the skilled person that EPO is a model protein for proteins comprising N-linked glycans, and it will thus be clear that these methods can also be applied to other glycosylated proteins. Further provided therefore is a method for producing a glycosylated protein of interest in a cell expressing at least one adenoviral E1A protein, the method comprising: a) providing a cell expressing at least one adenoviral E1A protein and further containing a nucleic acid encoding a protein of interest in expressible format, wherein the cell further contains a nucleic acid sequence encoding a sialyltransferase, preferably an α-2,6-sialyltransferase or an α-2,3-sialyltransferase, under control of a heterologous promoter; b) culturing the cell in a serum-free culture medium and allow expression of the protein of interest in the cell; c) harvesting the expressed protein of interest from the cell and/or from the culture medium; and d) purifying and fractionating the protein of interest to obtain fractions that have an increased average sialic acid content of the N-linked glycans per protein of interest molecule.

Further provided are methods to decrease the average content of LacdiNAc structures on a protein that is recombinantly expressed in a cell, the method comprising over-expressing an α-2,3-sialyltransferase in the cell. In certain embodiments, the cell is a eukaryotic cell containing a nucleic acid sequence encoding an adenoviral E1A protein in expressible format. In certain embodiments, the method further increases the average sialic acid content of the protein. In certain embodiments, the protein is erythropoietin.

DETAILED DESCRIPTION OF THE INVENTION

Figure 1:
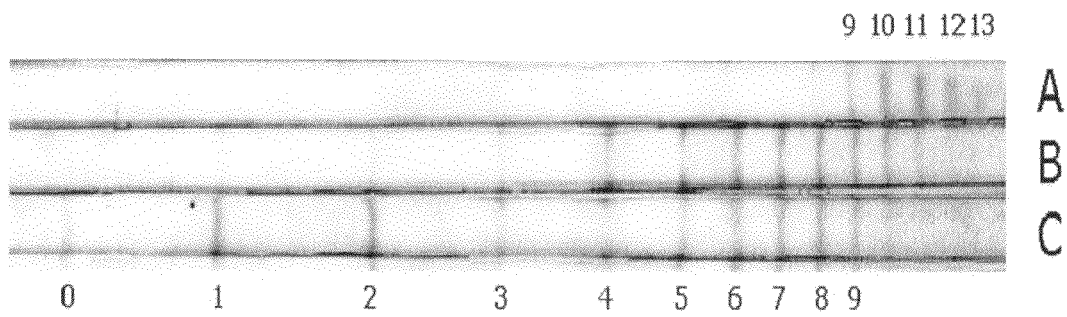
FIG. 1: Sialic acid content as determined by isoelectric focusing of commercially available EPO (EPREX™, lane A), EPO produced in PER.C6™-EPO-ST clone 25-3.10 (lane B), and EPO produced in PER.C6™-EPO clone 25 (lane C). The putative number of sialic acids per EPO molecule is also shown.

It has now been found and described herein that erythropoietin (EPO) (as a model protein for proteins containing N-linked glycans, when produced in E1A-expressing cells, of which PER.C6™ cells are a preferred example) compositions can be obtained with a strongly increased sialylation, and methods to obtain such EPO compositions are disclosed herein. Embodiments are disclosed providing methods to obtain EPO from E1A-expressing cells, wherein the EPO obtained contains a surprisingly high average sialic acid content per EPO molecule of between 13 and 15. Surprisingly, EPO with a similar in vivo biological activity as commercially available preparations can be obtained using methods according to the invention. This was an unexpected result given the hitherto described glycosylation profiles of EPO produced in E1A-expressing cells (WO 03/038100).

It is shown herein that the glycosylation of recombinant proteins expressed in E1A-expressing cells, such as immortalized human embryonic retina cells, can be altered to increase galactosylation and optionally sialylation, by metabolic and genetic engineering. This finding is put to practice in the present invention, by providing novel processes for the production of recombinant proteins in E1A-expressing cells, resulting in desired novel glycoforms of the produced proteins. The novel glycoforms of these proteins can be used for additional purposes when compared to the same proteins produced in such cells by the hitherto known processes.

In certain aspects, therefore, processes are provided for producing a protein of interest in a cell, the cell expressing at least an adenoviral E1A protein and expressing the protein of interest from a nucleic acid sequence encoding the protein of interest, the nucleic acid sequence being under control of a heterologous promoter, the cell further expressing at least one glycosyltransferase from a nucleic acid sequence encoding the glycosyltransferase under control of a heterologous promoter, the protein of interest comprising at least one N-linked glycan, the process comprising: culturing the cell in a serum-free culture medium preferably in suspension and allowing expression of the recombinant protein in the cell. The glycosyltransferase is preferably a mammalian glycosyltransferase, more preferably a human glycosyltransferase. In preferred embodiments, the glycosyltransferase is a sialyltransferase, preferably chosen from the group consisting of α-2,6-sialyltransferases and α-2,3-sialyltransferases.

Cells expressing E1A of an adenovirus that can be used and are encompassed within the scope of the terms "E1A-expressing cells" or "cells containing a nucleic acid sequence encoding an adenoviral E1A protein in expressible format" according to the invention are preferably mammalian cells and include cells of human origin, and are preferably immortalized. In preferred embodiments, these cells also express E1B of an adenovirus. Examples are A549 cells comprising E1 (see, e.g., WO 98/39411), 293 cells (Graham et al., 1977), amniocytes expressing E1 (Schiedner et al., 2000; see U.S. Pat. No. 6,558,948 for immortalization of primary amniocytes with adenovirus E1 sequences), and retina cells expressing E1 such as PER.C6™ cells (U.S. Pat. No. 5,994,128). They may preferably be derived from embryonic retina cells. Preferably, the cells according to the invention are human cells. The most preferred cells of the invention are derived from primary human retina cells (human embryonic retina cells, also referred to as HER cells). Immortalization of such cells with adenoviral E1 sequences has, for instance, been described in U.S. Pat. No. 5,994,128; in Byrd et al., 1982, 1988; and Gallimore et al., 1986. Primary HER cells can be isolated from fetuses (Byrd et al., 1982, 1988). Immortalized HER cells, including the preferred PER.C6™ cells, were generated by transfection of primary HER cells using a plasmid that contained the adenovirus serotype 5 (Ad5) E1A- and E1B-coding sequences (Ad5 nucleotides 459-3510) under the control of the human phosphoglycerate kinase ("PGK") promoter (see, U.S. Pat. No. 5,994,128).

In certain embodiments, the cells further contain nucleic acid encoding at least one adenoviral E1B protein, and preferably both E1B 55K and E1B 19K proteins, in expressible format. The expression of the E1B proteins may prevent apoptosis of the cells.

In order to achieve large-scale (continuous) production of recombinant proteins through cell culture, it is preferred to have cells capable of growing without the necessity of anchorage. The cells described herein have that capability. The most preferred cell for the methods and uses of the invention is a PER.C6™ cell. PER.C6™ cells for the purpose of the present application shall mean cells from an upstream or downstream passage or a descendent of an upstream or downstream passage of cells as deposited under ECACC No. 96022940, deposited on Feb. 29, 1996 with the ECACC, CAMR, Salisbury, Wiltshire, SP4 OJG, United Kingdom (see, e.g., U.S. Pat. No. 5,994,128). PER.C6™ cells behave better in handling than, for instance, transformed human 293 cells that have also been immortalized by the E1 region from adenovirus. PER.C6™ cells have been characterized and have been documented very extensively because they behave significantly better in the process of up-scaling, suspension growth and growth factor independence. The fact that PER.C6™ cells can be brought in suspension in a highly reproducible manner make them especially suitable for large-scale production. Furthermore, the PER.C6™ cell line has been characterized for bioreactor growth in which it grows to very high densities. Use of PER.C6™ cells for industrial processes has been extensively described, e.g., in Nichols et al., 2002, and more, in particular, for recombinant protein production, e.g., in Yallop et al., 2005a and 2005b.

These cells, in particular PER.C6™ cells, have the additional advantage that they can be cultured in the absence of animal- or human-derived serum or animal- or human-derived serum components. Thus, isolation is easier, while the safety is enhanced due to the absence of additional human or animal proteins in the culture, and the system is very reliable (synthetic media are the best in reproducibility). In addition, the use of serum-free culture medium can have a positive influence on the glycosylation pattern of the recombinant protein produced, as shown herein.

Furthermore, the presence of the Early region 1A ("E1A") of adenovirus adds another level of advantages as compared to (human) cell lines that lack this particular gene. E1A as a transcriptional activator is known to enhance transcription from the enhancer/promoter of the CMV Immediate Early genes (Olive et al., 1990; Gorman et al., 1989). When the recombinant protein to be produced is under the control of the CMV enhancer/promoter, expression levels increase in the cells and not in cells that lack E1A. The expression of E1A influences the glycosylation of proteins produced in such cells (WO 03/038100).

N-linked glycans are sugar chains that are covalently linked to asparagine residues of a polypeptide (Varki et al. 1999). The process of N-glycosylation starts with the attachment of a dolichol oligosaccharide precursor to the asparagines precursor. This precursor is subsequently modified into a high-mannose, hybrid, or complex-type oligosaccharide. In complex type N-linked sugars, both the $\alpha$-3- and $\alpha$-6-linked mannose residues are substituted by N-acetyl-glucosamine (GlcNAc) residues. Complex type N-glycans may contain two to five GlcNAc-bearing branches that are referred to as antennae. The ultimate structure of complex type N-linked sugars may vary extensively and depends on the protein to which they are attached, on the host cell and on the conditions under which the host cell is cultured. The GlcNAc-bearing branches may be modified with galactose (Gal) or N-acetyl-galactosamine (GalNAc) forming so-called LacNAc or LacdiNAc structures. Also, GlcNAc-bearing branches may contain multiple LacNAc structures forming so-called polylactosamine structures. Terminal galactoses may be modified with an $\alpha$-2,3- or an $\alpha$-2,6-linked sialic acid, whereas terminal N-acetyl-galactosomines may only be modified with an $\alpha$-2,6-linked sialic acid.

The addition of sialic acids to terminal Gal or GalNAc is mediated by sialyltransferases. Probably more than 20 different sialyltransferases are encoded by the human genome (Harduin-Lepers et al., 2001). They differ in substrate specificity, tissue distribution and various biochemical parameters. No human sialyltransferase has today been described that can link a sialic acid to a LacNac or LacdiNAc structure, which is modified with an $\alpha$-1,3-linked fucose. Such fucose is linked to the GlcNAc residue, thereby forming a so-called Lewis x structure. Sialylated Lewis x (sialyl-Lewis x) structures, nevertheless, may exist; yet, these are formed through a process in which the sialic acid is attached to the sugar before the GlcNAc is modified with the $\alpha$-1,3-linked fucose. The formation of sialyl-Lewis x structures depends, in turn, on the type of fucosyltransferase. Some fucosyltransferases use only non-sialylated LacNac or LacdiNAc structures as a substrate, others only use sialylated LacNAc as a substrate, and a third group of $\alpha$-1,3 fucosyltransferases may use both as a substrate.

Recombinant proteins, such as recombinant human EPO, produced in E1A-expressing cells such as PER.C6™ cells, may sometimes be poorly sialylated due to a low incorporation of Gal and due to the presence of $\alpha$-1,3-linked fucoses. Provided herein is a method to increase the sialic acid content of proteins produced in E1A-expressing cells such as PER.C6™ cells. The increased level of sialylation is obtained in two steps: the first step involves the increase in the level galactosylation in order to provide more (acceptor) sites for sialylation. An increase in the level of galactosylation was found to occur when PER.C6™ cells were adapted for growth in suspension in a serum-free culture medium. The second step involves the increase in the cell's potential to catalyze the process of sialylation, which was accomplished by the over-expression of a sialyltransferase. Because the N-linked sugars of recombinant proteins expressed in PER.C6™ cells may contain LacdiNAc structures, which may only be modified with an $\alpha$-2,6-linked sialic acid, an $\alpha$-2,6-sialyltransferase was first used to increase the level of sialylation. However, as shown below, it was surprisingly found and disclosed herein that an $\alpha$-2,3-sialyltransferase could also be used, and that this resulted in a reduction of the LacdiNAc structures on the protein produced.

Thus, two aspects appear relevant for increasing sialylation of produced proteins in cells that express adenovirus E1A protein: improvement of the galactosylation to increase the number of substrates for sialylation, and increasing the sialylation of the available Gal and GalNAc substrates. The invention has improved the hitherto described protein production process in E1A-expressing immortalized HER cells by over-expressing a glycosylation enzyme, preferably a sialyltransferase, in these cells (genetic engineering), and by culturing such cells in serum-free medium, preferably in suspension (metabolic engineering). By combining these measures, the forming of mature N-linked sugars that are sialylated can be dramatically improved over the hitherto described production processes in the absence of over-expression of a glycosyltransferase and performed in cells that have been cultured in a serum-containing medium in an adherent fashion. Each of the two measures, i.e., over-expression of an enzyme involved in post-translational modification of proteins on the one hand, and the growth of the cells in serum-free culture medium in suspension culture, contributes to the improved final result and, hence, the invention also comprises embodiments where only one of the two measures is taken at a time. When proteins with N-linked sugars having a high degree of galactosylation and terminal sialylation are desired, it is best to combine these measures according to the invention.

These measures can be used to increase the sialylation of the N-linked sugars of any protein comprising N-linked sugars produced in the cells of the invention. In one embodiment, EPO or a fragment, a mutein, or a derivative thereof, is the protein of interest that is produced according to the method of the invention. EPO produced according to this process has a higher sialic acid content than the EPO produced thus far in cells that express E1A of an adenovirus and, hence, more resembles the commercially available EPO preparations. Commercial EPO preparations are usually recombinantly produced in CHO or BHK cells, and fractions containing a high degree of sialylation are isolated, because increased sialylation is beneficial for the half-life of the protein and, therefore, for the capability to exert its therapeutic effect of increasing hemoglobin and red blood cell counts. Hence, the new cells and process according to the invention provide the possibility to use cells that express E1A, such as human embryonic retina cells that express E1A, such as PER.C6™ cells, for the recombinant production of EPO with increased half-life. In addition, the method benefits from the high level of production that is possible in the cells according to the invention.

Of course, the EPO or other proteins produced in the E1A-expressing cells that over-express a sialyltransferase can be fractionated to obtain further fractions with still higher sialic acid contents, as is also done for commercial preparations of EPO. In one aspect, the EPO produced according to the invention, is purified using an anion exchange column to obtain highly sialylated fractions. It is shown herein that EPO can be obtained from E1A-expressing cells, in particular from E1A expressing immortalized HER cells, with a surprisingly high average sialic acid content using such methods.

Methods to produce proteins in host cells are well established and known to the person skilled in the art. The use of E1A-expressing HER cells for this purpose is described in WO 00/63403.

In general, the production of a recombinant protein in a host cell comprises the introduction of nucleic acid in expressible format into the host cell, culturing the cells under conditions conducive to expression of the nucleic acid and allowing expression of the nucleic acid in the cells.

Alternatively, a protein that is naturally expressed in desired host cells, but not at sufficient levels, may be expressed at increased levels by introducing suitable regulation sequences such as a strong promoter in operable association with the desired gene (see, e.g., WO 99/05268, where the endogenous EPO gene is over-expressed by introduction of a strong promoter upstream of the gene in human cells).

The protein may be expressed intracellularly, but it may be secreted into the culture medium. Naturally secreted proteins, such as many proteins of interest for pharmaceutical applications, contain secretion signals that bring about secretion of the produced proteins. If desired, secretion signals may also be added to certain proteins by methods known in the art.

Nucleic acid encoding a protein in expressible format may be in the form of an expression cassette, and usually requires sequences capable of bringing about expression of the nucleic acid, such as enhancer(s), promoter, polyadenylation signal, and the like. Several promoters can be used for expression of recombinant nucleic acid, and these may comprise viral, mammalian, synthetic promoters, and the like. In certain embodiments, a promoter driving the expression of the nucleic acid of interest is the CMV immediate early promoter, for instance, comprising nt. −735 to +95 from the CMV immediate early gene enhancer/promoter, as this promoter has been shown to give high expression levels in cells expressing E1A of an adenovirus (see, e.g., WO 03/051927). The nucleic acid of interest may be a genomic DNA, a cDNA, synthetic DNA, a combination of these, etc.

Cell culture media are available from various vendors, and serum-free culture media are nowadays often used for cell culture, because they are more defined than media-containing serum. The cells of the present invention grow well in serum-containing media as well as in serum-free media. Usually a short period is required to adapt PER.C6™ cells from a serum-containing medium, such as DMEM+9% FBS, to a serum-free medium. One example of a serum-free culture medium that is very suitable for use in the present invention is EX-CELL™ VPRO medium (JRH Biosciences, catalog number 14561). Another example is HyQ® CDM4Retino™ (HyClone). Other serum-free media are available and can be used as well. The cells of the invention in general grow adherently in serum-containing media, but are very proficient in growing in suspension to high cell densities ($10 \times 10^6$ cells/ml and higher) in serum-free culture media, which means that they do not need a surface to adhere to, but remain relatively free from each other and from the walls of the culture vessel during most of the time. Processes for culturing the cells of the invention to high densities and/or for obtaining very high product yields from these cells have been described (WO 2004/099396).

The concept of genetic engineering to alter glycosylation of recombinant proteins produced in a cell has been amply established and is, for instance, discussed in detail in U.S. Pat. No. 5,047,335. The general concept of genetically altering glycosylation is discussed therein and entails introducing into a host cell at least one gene that is capable of expressing at least one enzyme that is selected from the group consisting of glycosyltransferases, fucosyltransferases, galactosyltransferases, β-acetylgalactosaminyltransferases, N-acetylglycosaminyltransferases and sulfotransferases (collectively referred to herein as "glycosylation enzymes"), and expressing a sufficient amount of at least one of the enzymes in the cell to thereby alter the glycosylation of a protein produced by the cell. In examples in that document, glycosylation of CHO cells is altered by recombinant expression of a transfected rat α-2,6-sialyltransferase gene, resulting in the presence of NeuAc-α-2,6Gal sequences on the cell surface carbohydrates, whereas in the absence of the transfected gene, only NeuAc-α-2,3Gal sequences are produced in these cells. Subsequent work has established that glycosylation engineering is applicable to the production of recombinant proteins in host cells (e.g., Grabenhorst et al., 1995; Minch et al., 1995; Jenkins et al., 1998; Zhang et al., 1998; Weikert et al., 1999; Fukuta et al., 2000; Prati et al., 2000). Hence, the methods for genetic engineering of glycosylation as such are well established and known to the person skilled in the art, and can as such be beneficially used according to the present invention. It is shown herein that E1A-expressing cells can also be genetically engineered and compositions of recombinant EPO protein, as a model for glycosylated proteins, with surprisingly high average sialic acid content can thus be obtained.

To this purpose, nucleic acid encoding the desired glycosylation enzyme in expressible format is or has been introduced into the cells according to the invention, and the desired glycosylation enzyme is expressed during the culturing of the cells according to the invention when the protein of interest is expressed. This results in an altered glycosylation pattern of the protein of interest as compared to the situation when no recombinant glycosylation enzyme is expressed in the cells. In preferred embodiments, the glycosylation enzyme is a sialyltransferase, more preferred an α-2,3-sialyltransferase and/or an α-2,6-sialyltransferase. Preferably, the encoded glycosylation enzyme is a mammalian enzyme, more preferably a human enzyme. The nucleic acid encoding the desired glycosylation enzyme preferably is under control of a heterologous promoter, which should be active or have the possibility of being regulated in the cells of the invention. Preferably, the nucleic acid encoding the glycosylation enzyme is integrated into the genome of the cells to ensure stable inheritance and provide for stable expression of the enzyme in subsequent generations of the cells. The introduction of a glycosylation enzyme into immortalized HER cells expressing E1A is described herein. As can be seen from the examples, the expression of the sialyltransferase increases the sialylation of recombinant proteins in those cells. Moreover, when the E1A-expressing cells expressing the sialyltransferase are grown in suspension in serum-free culture media according to the present invention, a clear and significant increase in sialylation of the N-linked glycans of a recombinant protein that is expressed in these cells is observed, as can be seen in Example 3 below. Hence, in preferred embodiments of the processes according to the present invention, the cells according to the invention comprise nucleic acid encoding a glycosylation enzyme, preferably a sialyltransferase, such as α-2,6-sialyltransferase, in expressible format, for instance, under control of a heterologous promoter, i.e., a promoter that is not the natural promoter of the gene encoding the glycosylation enzyme. A suitable α-2,6-sialyltransferase is a human α-2,6-sialyltransferase, the sequence of which was described by Grundmann et al., 1990.

In another preferred embodiment, the cells comprise nucleic acid encoding an α-2,3-sialyltransferase, in expressible format, for instance, under control of a heterologous promoter. The α-2,3-sialyltransferase may, for instance, be a human α-2,3-sialyltransferase, known as SIAT4C or STZ (GenBank accession number L23767, see also U.S. Pat. No. 5,494,790).

As described above and in WO 03/038100, EPO molecules comprising Lewis x structures can be suitably produced in cells that express adenovirus E1A sequences, such as PER.C6™ cells. A Lewis x structure, as present on an N-linked glycan of a glycoprotein such as EPO, is a structure that comprises an α-1,3-linked fucose attached to N-acetyl-glucosamine in a lactosamine-type antenna structure. There are two types of Lewis x structures: one with a terminal galactose and one with a terminal N-acetylgalactosamine (GalNAc) residue. These terminal groups may or may not be linked to a sialic acid; when linked to a sialic acid, the Lewis x structure is a sialyl-Lewis x structure. Hence, sialyl-Lewis x structures are a subgroup of Lewis x structures for the purpose of the present invention. One advantage of having a protein comprising N-linked glycans with Lewis x structures, described in WO 03/038100, is that such structures may aid the protein in binding to certain selectins and provide anti-inflammatory properties. As discussed hereinabove, however, it would also be beneficial if such proteins would comprise increased terminal sialylation, to increase the serum half-life and, hence, effectiveness of the protein for certain therapeutic applications.

As an example, EPO produced in PER.C6™ cells as described in WO 03/038100 comprises Lewis x structures, but only a low level of sialic acid (see, Example 8, Table 4). The methods described in the present invention provide the possibility to obtain protein molecules comprising Lewis x structures, and increased numbers of sialic acid moieties attached to their sugar structures.

The invention therefore provides a composition comprising one or more isoforms of an erythropoietin- (EPO-) comprising glycans linked thereto, wherein the glycans comprise on average: a) at least one Lewis x structure per EPO molecule, and b) at least six sialic acid moieties per EPO molecule. A mixture of such isoforms can be obtained by producing EPO in PER.C6™ cells that further over-express a sialyltransferase and that is cultured in suspension in serum-free medium. Previously disclosed methods (WO 03/038100) for producing EPO in PER.C6™ cells lead to EPO that comprise Lewis x structures but significantly lower amounts of sialic acids (see, entry 1 in Table 4). The composition is generally obtained as a mixture of EPO isoforms, but the person skilled in the art could isolate the separate isoforms, as described in U.S. Pat. No. 5,856,298, in particular, Example 1 therein. In certain embodiments, the composition comprises on average at least seven sialic acid moieties per EPO molecule, more preferably at least eight sialic acid moieties per EPO molecule. The sialic acid moieties are mainly present as terminal sialic acids on N-linked glycans, but some sialic acids might be present on O-linked glycans and contribute to the average sialic acid content of the composition. In certain embodiments, the EPO molecule of the invention comprises three N-linked glycans. In certain embodiments, the EPO molecule of the invention comprises three N-linked glycans and one O-linked glycan. The Lewis x structures are present on N-linked glycans of the EPO molecules. It is shown herein that upon expression in PER.C6™ cells that over-express a sialyltransferase and that are cultured in suspension in serum-free medium, a composition of EPO molecules is obtained that has, on average, about 1.2-1.8 Lewis x structures and about nine sialic acids per EPO molecule (see, entry 2 in Table 4). In certain embodiments, the invention therefore provides a composition comprising one or more isoforms of an erythropoietin- (EPO-) comprising glycans linked thereto, wherein the glycans comprise, on average: a) between one and two Lewis x structures per EPO molecule, and b) between eight and ten sialic acid moieties per EPO molecule.

Such compositions can be used to further purify and obtain even more preferred compositions, having average sialic acid content that is still higher. The invention therefore also provides a composition comprising one or more isoforms of an erythropoietin- (EPO-) comprising glycans linked thereto, wherein the glycans comprise, on average: a) at least 0.5 Lewis x structure per EPO molecule, and b) at least ten sialic acid moieties per EPO molecule. Preferably, such compositions comprise, on average, at least 11 sialic acid moieties per EPO molecule. It is shown herein that upon separation, EPO fractions can be obtained that comprise on average about 0.6 Lewis x structure and about 12.6 sialic acid moieties per EPO molecule (see, entry 3 in Table 4). In certain embodiments, the invention therefore provides a composition comprising one or more isoforms of an erythropoietin- (EPO-) comprising glycans linked thereto, wherein the glycans comprise, on average: a) between 0.5 and one Lewis x structure per EPO molecule, and b) between 11 and 13 sialic acid moieties per EPO molecule. For comparison, a commercially available EPO preparation analyzed in the same manner does not comprise Lewis x structures and, on average, contained about 12.4 sialic acids per EPO molecule (see, entry 4 in Table 4).

The invention provides still more preferred compositions of EPO, which comprise, on average, less than one, preferably less than 0.5, more preferably less than 0.3 Lewis x structure, and in preferred embodiments, comprise no Lewis x structure (or at least below detection limits using the methods as disclosed herein), while further, on average, comprising between 12 and 15, more preferably between 13 and 15 sialic acids per EPO molecule. In certain embodiments, the EPO, on average, contains less than 0.3 Lewis x structure, down to no detectable Lewis x structure using the methods disclosed herein, and between 14 and 15 sialic acids per EPO molecule.

The compositions according to the invention preferably comprise five or less EPO isoforms, together accounting for at least 70%, preferably at least 80%, of the EPO present in the composition, more preferably four or less EPO isoforms together accounting for at least 70%, preferably at least 80%, of the EPO present in the composition.

The described EPO compositions can be prepared according to the methods disclosed herein, and it is possible according to the invention to obtain a variety of EPO compositions, which vary as to the extent of their in vivo biological activity, from less than 10% to around 100% of the EPO BRP standard or commercially available EPO preparations. In certain embodiments, the EPO thus obtained has between 1% and 20% in vivo biological activity as measured according to the Pharmacopoeia (PHEUR) standard method. In other embodiments, preparations are obtained wherein these values are between 20% and 40% and in yet other embodiments, these values are between 40% and 120%, preferably between 60% and 120%, more preferably between 80% and 120%. It is thus possible to provide a spectrum of EPO preparations with differing in vivo biological erythropoietic activity, and/or differing pharmacokinetics. The lower erythropoietic forms (with relatively low sialic acid content) may be suitably used for cytoprotective purposes, while the higher erythropoietic forms (with relatively high sialic acid content) are suitable for both erythropoietic as well as for cytoprotective purposes. For the latter purpose, the higher sialylated forms may advantageously be used because of their increased half-life and improved pharmacokinetic properties, while at the same time, the erythropoietic activity may or may not be impaired. An example of an EPO having impaired erythropoietic activity is an EPO mutein as described by Leist et al. (2004), e.g., EPO S100E or R103E, having no significant erythropoietic activity but still being active in cytoprotection. Such EPO could also be beneficially prepared according to the methods disclosed herein, thereby improving the half-life after administration.

An erythropoietin preferably is human erythropoietin, a fragment of human erythropoietin, or a mutein of human erythropoietin. Such an erythropoietin should preferably be biologically active, which means that it should have at least one of the following activities: a) causing bone marrow cells to increase production of reticulocytes and red blood cells, increase hemoglobin synthesis or iron uptake (see, e.g., U.S. Pat. No. 4,703,008) (collectively referred to as "erythropoietic activity"), and/or b) responsive cellular protective activity selected from the group consisting of protecting, maintaining, enhancing or restoring the function or viability of a responsive mammalian cell, tissue or organ (sometimes collectively referred to herein as "cytoprotective activity"), such as, for instance, disclosed in WO 00/61164 and WO 02/053580. The sequence of human erythropoietin is well known (e.g., U.S. Pat. No. 5,441,868; EP patent 0411678; cDNA: Genbank accession number: MI 1319). EPO muteins, analogues, peptides, or fragments binding the EPO receptor and having some kind of activity associated with EPO have, for instance, been described in U.S. Pat. Nos. 5,457,089, 4,835,260, 5,767,078, 5,856,292, 4,703,008, 5,773,569, 5,830,851, 5,835,382, and international publications WO 95/05465, WO 97/18318 and WO 98/18926, all incorporated by reference for the purpose of, e.g., disclosing EPO fragments and EPO muteins having biological activity. The EPO of the invention may also be modified, as, for instance, disclosed in WO 02/053580, e.g., by carbamylation of one or more lysines in the EPO molecule (see, e.g., WO 02/053580; Leist et al., 2004): such modified EPO has no erythropoietic activity, but retains its tissue-protective activity. Certain EPO mutants have also been found to have these properties (Leist et al., 2004), such as EPO with a mutation of serine to glutamate at position 100 (EPO-S100E) and EPO with a mutation of arginine to glutamate at position 103 (EPO-R103E). Lists of these and other EPO mutants have been disclosed in WO 2004/003176, incorporated herein by reference. All these modified EPO molecules and all these muteins are included within the scope of an erythropoietin according to the present invention. In certain embodiments, EPO is human EPO, which contains four carbohydrate chains. Three of these contain N-linkages to asparagines, and one contains an O-linkage to a serine residue. The importance of glycosylation in the biological activity of EPO has been well documented (Delorme et al. 1992; Yamaguchi et al. 1991).

The EPO compositions described above can be obtained using the novel methods disclosed herein. The invention therefore further provides a method for obtaining a composition comprising one or more isoforms of an EPO-comprising glycans linked thereto wherein the glycans comprise, on average, at least six sialic acids per EPO molecule and from zero to two Lewis x structures, the method comprising: a) providing a eukaryotic cell containing a nucleic acid sequence encoding an adenoviral E1A protein in expressible format and further containing a nucleic acid encoding EPO in expressible format, wherein the cell further contains a nucleic acid sequence encoding a sialyltransferase, preferably an $\alpha$-2,6-sialyltransferase or an $\alpha$-2,3-sialyltransferase, under control of a heterologous promoter; b) culturing the cell in a serum-free culture medium and allow expression of an EPO in the cell; c) harvesting the expressed EPO from the cell and/or from the culture medium; and d) purifying and fractionating the EPO to obtain fractions that have an increased average sialic acid content of the N-linked glycans per EPO molecule, to obtain a composition comprising one or more isoforms of an EPO-comprising glycans linked thereto wherein the glycans comprise, on average, at least six sialic acids per EPO molecule and from zero to two Lewis x structures. The sialyltransferase and the E1A protein are also expressed during the culturing of the cells. In certain embodiments of this method, no Lewis x structures are detected in the EPO composition using methods exemplified herein, meaning that, on average, in a MALDI-MS spectrum of the N-linked glycans isolated from the composition, no peaks with an intensity of 10% or higher comprise a Lewis x structure. In certain embodiments, less than 5%, and in certain other embodiments, none of the glycans in the EPO preparations obtained comprise Lewis x structures. In other embodiments, one of the various EPO compositions described herein above is obtained.

Methods to purify and further fractionate EPO compositions, enriching for EPO that, on average, has an increased sialic acid content per EPO molecule (step d of the methods according to the invention), are known to the person skilled in the art and include, for instance, anion exchange chromatography, preparative isoelectric focusing (IEF), chromatofocusing, affinity chromatography, e.g., using lectins, capillary zone electrophoresis (CZE), etc.

As an additional advantage of engineering a cell line according to the invention, e.g., by over-expression of a glycosyltransferase, the antennarity of the glycans present on the proteins produced by the engineered cells is, in general, increased, i.e., in general, there are more tri- and tetra-antennary structures present. Further, the complexity (heterogeneity) of the glycans on the proteins thus produced is generally reduced. This is advantageous because increased antennarity may improve half-life and/or biological activity of a protein such as EPO (Takeuchi et al., 1989), and for regulatory and economic purposes, a less complex mixture of glycans on the produced proteins in a process is desirable. Hence, the invention also provides a method for increasing the antennarity and/or reduce the heterogeneity of glycans of proteins that are recombinantly produced in a cell, the method being characterized by over-expressing a sialyltransferase in the cell. In certain embodiments, the cell is a cell expressing E1A of an adenovirus, such as an HER cell expressing E1A, such as a PER.C6™ cell. In certain embodiments, the glycosyltransferase is a sialyltransferase, which, in certain embodiments, is chosen from an $\alpha$-2,3-sialyltransferase and an $\alpha$-2,6-sialyltransferase. The sialyltransferase may be a human sialyltransferase, for instance, the human $\alpha$-2,3-sialyltransferase known as SIAT4C or STZ (GenBank accession number L23767, see also U.S. Pat. No. 5,494,790).

It was unexpectedly observed that the glycosylation engineering as described herein provided robust cell culture processes, in that the quality of glycosylation of the recombinant protein so produced did not significantly change upon changing the cell culture conditions, while for non-engineered cells, usually the changing of culture conditions leads to a decrease in glycosylation quality. In one aspect, therefore, a method is provided to increase the robustness of a process for recombinant expression of a glycoprotein in a cell, the method being characterized by over-expressing a sialyltransferase in the cell. In certain embodiments, the cell is a cell expressing E1A of an adenovirus, such as an HER cell expressing E1A, such as a PER.C6™ cell. In certain embodiments, the glycosyltransferase is a sialyltransferase, which, in certain embodiments, is chosen from an α-2,3-sialyltransferase and an α-2,6-sialyltransferase. The sialyltransferase may be a human sialyltransferase, for instance, the human α-2,3-sialyltransferase known as SIAT4C or STZ (Genbank accession number L23767; see also U.S. Pat. No. 5,494,790).

In addition, it is shown herein contrary to expectation, that a cell expressing E1A of an adenovirus, such as a PER.C6™ cell, producing a recombinant protein that normally comprises in its glycans so-called LacdiNAc structures when expressed in such cells, can, by over-expression of an α-2,3-sialyltransferase, be engineered such that high levels of sialylation on the produced protein are observed while no LacdiNAc structures are observed. This is unexpected, since the formation of the LacdiNAc structure was thought to occur independently of sialylation. In fact, LacdiNAc is formed prior to the potential addition of sialic acid. The novel finding described herein thus indicates that the over-expression of an α-2,3-sialyltransferase indirectly inhibits the formation of LacdiNAc structures. The invention therefore provides a method to decrease the average content of LacdiNAc structures and optionally increasing the average content of sialic acid on proteins recombinantly expressed in a cell, the method comprising over-expressing an α-2,3-sialyltransferase in the cell. In certain embodiments, the cell is a eukaryotic cell expressing E1A of an adenovirus, such as an HER cell expressing E1A, such as a PER.C6™ cell. The over-expression of the sialyltransferase can be brought about as described above. The over-expression of the sialyltransferase is together with the expression of the protein of interest in the cell, during culturing the cells as described above. The protein of interest is a protein that contains at least one N-linked glycan when expressed. When expressed in the cell type, it contains at least a detectable amount of LacdiNAc structures on its N-linked glycan(s), e.g., at least one LacdiNAc structure on at least one N-linked glycan of at least 10% of the protein so produced. Preferably, the decrease in the average content of LacdiNAc structures on the protein is at least 20%, more preferably at least 50%, still more preferably at least 80%. Most preferably, the decrease is such that the resulting protein contains no detectable amount of LacdiNAc structures on its N-linked glycans, using the methods described herein, e.g., on average, in a MALDI-MS spectrum of the N-linked glycans isolated from the protein, no peaks with an intensity of 10% or higher comprise a LacdiNAc structure. The sialyltransferase is preferably encoded by nucleic acid encoding the α-2,3-sialyltransferase under control of a heterologous promoter, which nucleic acid preferably is integrated into the genome of the cell. The sialyltransferase for this aspect of the invention in certain embodiments is a human α-2,3-sialyltransferase, such as the one known as SIAT4C or STZ (Genbank accession number L23767; see also U.S. Pat. No. 5,494,790).

To illustrate the invention, the following examples are provided, not intended to limit the scope of the invention.

EXAMPLES

Example 1

Increased Sialylation of EPO Produced in PER.C6™ Cells by the Over-Expression of α-2,6-sialyltransferase To determine the effect of over-expression of α-2,6-sialyltransferase on the sialylation of EPO produced in PER.C6™ cells, EPO was produced in adherent cultures of an α-2,6 sialyltransferase over-expressing PER.C6™ cell line, i.e., PER.C6™-EPO-ST clone 25-3.10 (see, Example 2 of WO 03/048348, incorporated by reference), and in the parental cell line PER.C6™-EPO clone 25 not over-expressing the α-2,6-sialyltransferase. The cells were first cultured in T-flasks in DMEM+10 mM $MgCl_2$+9% FBS. At the moment that the cells were grown to 60-70% confluency, the serum-containing medium was replaced by DMEM+10 mM $MgCl_2$ without serum. The culture was then continued at 37° C. and 10% $CO_2$ for three to four days. The culture supernatant was thereafter harvested and EPO was purified and analyzed using methods that have been described in WO 03/038100, the contents of the entirety of which are incorporated by this reference. The sialic acid content of the EPO produced by the PER.C6™-EPO-ST clone 25-3.10 and its parental cell line was determined by isoelectric focusing. As can be observed from the results shown in FIG. 1, the sialic acid content of the EPO produced in PER.C6™ cells over-expressing the α-2,6-sialyltransferase was higher than that of EPO produced in the parental PER.C6™ cell line in which the α-2,6-sialyltransferase was not over-expressed, indicating that the over-expression of the α-2,6-sialyltransferase results in an increased sialylation of the PER.C6™-produced EPO.

Example 2

Increased Level of Galactosylation and Fucosylation of EPO Produced in Per.C6™ Cells Through the Adaptation of the Cells to Growth in Suspension in Serum-Free Medium The stable PER.C6™ cell line, PER.C6™-022, producing EPO was used to assess the level of galactosylation of EPO when the cells were cultured adherently (using methods described in Example 1) and when the cells were adapted to growth in serum-free medium. For the latter, a procedure was developed to produce EPO in PER.C6™ cells that were cultured in suspension in serum-free medium. The procedure is described below and was applied to several EPO-producing PER.C6™ cell lines. PER.C6™-EPO-022 cells were used to produce EPO with N-linked glycans structures that are typical for non-modified PER.C6™ cells as described in WO 03/038100.

For the production of PER.C6™-EPO, the above-indicated cell line was adapted to a serum-free medium, i.e., Excell 525 (JRH Biosciences). Therefore, the cells were first cultured to form a 70%-90% confluent monolayer in a T80 culture flask in DMEM+9% FBS+10 mM $MgCl_2$ and thereafter washed with PBS and trypsinized according to routine culture techniques. The cells were subsequently suspended in DMEM+9% FBS+10 mM $MgCl_2$ and centrifuged for five minutes at 1000 rpm in a table centrifuge. The supernatant was discarded and the cells were re-suspended in the serum-free medium, Excell 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $\geq 1 \times 10^6$ cells/ml, the cells were sub-cultured. Therefore, the cells were spun down for five minutes at 1000 rpm and suspended in fresh Excell 525+4 mM L-Glutamine to a cell density of 0.2 or $0.3 \times 10^6$ cells/ml and further cultured in shaker flasks at 37° C., 5% $CO_2$ and 100 rpm.

For production of EPO, the cells were transferred to a serum-free production medium, i.e., VPRO (JRH Biosciences), which supports the growth of PER.C6™ cells to very high cell densities (usually >$10^7$ cells/ml in a batch culture). For this purpose, the cells were first cultured to ≧1×10⁶ cells/ml in Excell 525, then spun down for five minutes at 1000 rpm and subsequently suspended in VPRO medium+6 mM L-glutamine to a density of 1×10⁶ cells/ml. The cells were then cultured in a shaker flask for seven to ten days at 37° C., 5% $CO_2$ and 100 rpm. During this period, the cells grew to a density of >10⁷ cells/ml. The culture medium was harvested after the cell viability started to decline. The cells were spun down for five minutes at 1000 rpm and the supernatant was used for the quantification and purification of EPO. The concentration of EPO was determined using ELISA (R&D Systems) and turned out to be 14,044 eU/ml for the EPO produced by PER.C6™-EPO-022. Thereafter, EPO was purified by affinity chromatography using an anti-EPO antibody as previously described (WO 03/038100, incorporated by reference).

The composition of the N-linked glycans on EPO produced by PER.C6™ cells was analyzed using MALDI-MS. Therefore, glycoprotein samples were concentrated and buffer-exchanged to 20 mM sodium phosphate (pH 7.2) using Millipore Microcon 10 concentrators, obtaining a final concentration of approximately 1 μg/μl. Subsequently, the glycoprotein was digested with PNGase F, which releases the N-linked glycans and the samples were incubated with neuraminidase, which removes the sialic acid residues. The desialylated glycan pool was analyzed without further purification using MALDI-MS. Positive ion MALDI-MS was performed on an Applied Biosystems Voyager DE Pro mass spectrometer in the reflector mode; 2,5-dihydroxybenzoic acid was used as a matrix (DHB, 10 mg/ml in 50/50/0.1 acetonitrile/water/trifluoroacetic acid).

Spectra obtained with the above-described procedures were smoothed using the functions and parameters in the Data Explorer software. First, a baseline correction was performed on the spectra using the advanced baseline correction tool (peak width 32, flexibility 0.5, degree 0.1). After this step, the function Noise Removal (std. dev. to remove=2) was used to reduce the noise in the spectrum.

Figure 2A:
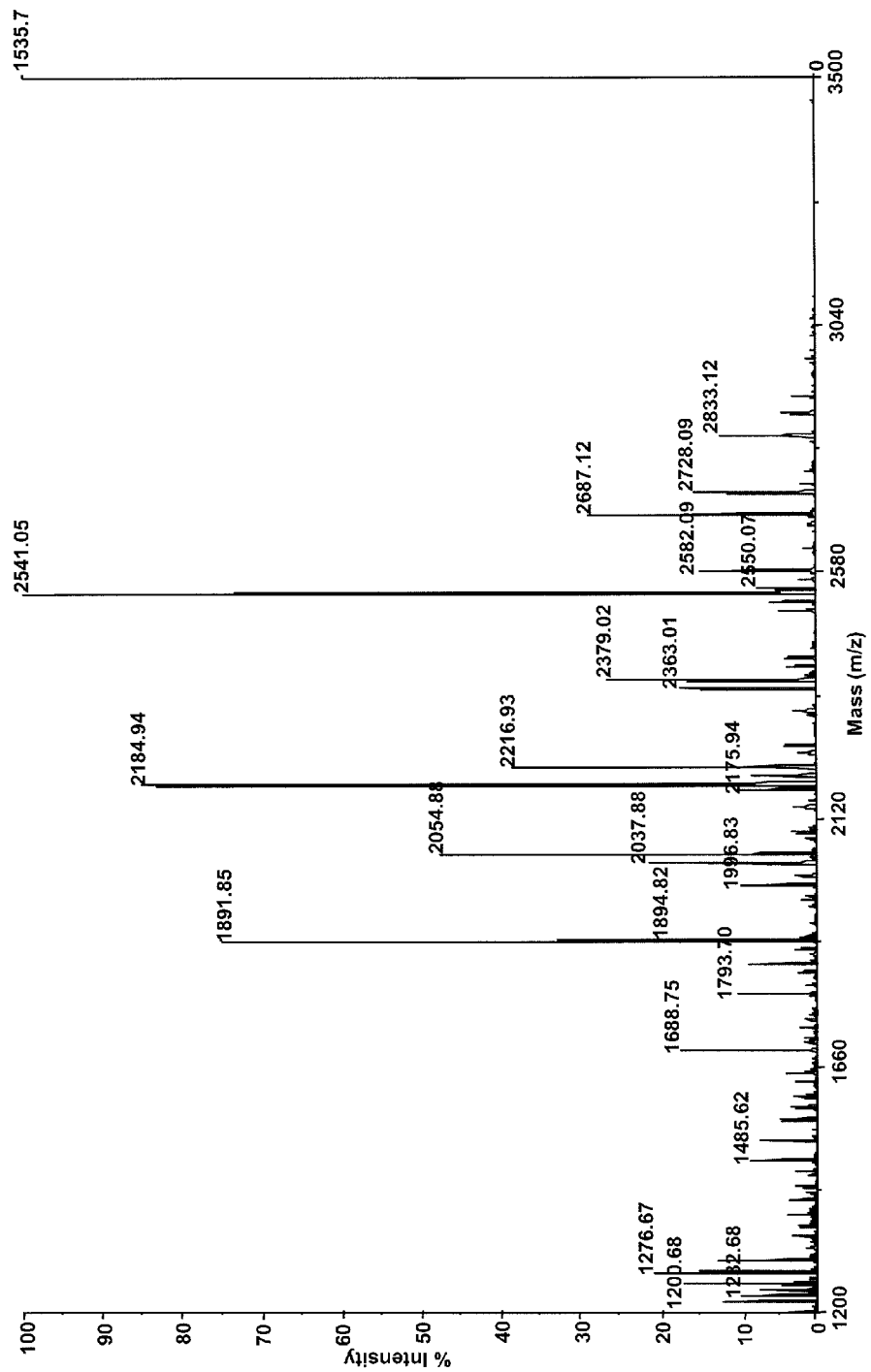
FIG. 2: MALDI-MS spectra of de-sialylated N-linked sugars of PER.C6™-EPO produced in DMEM, in adherent cell culture (A) and produced in a suspension cell culture in serum-free medium (B).
Figure 2:
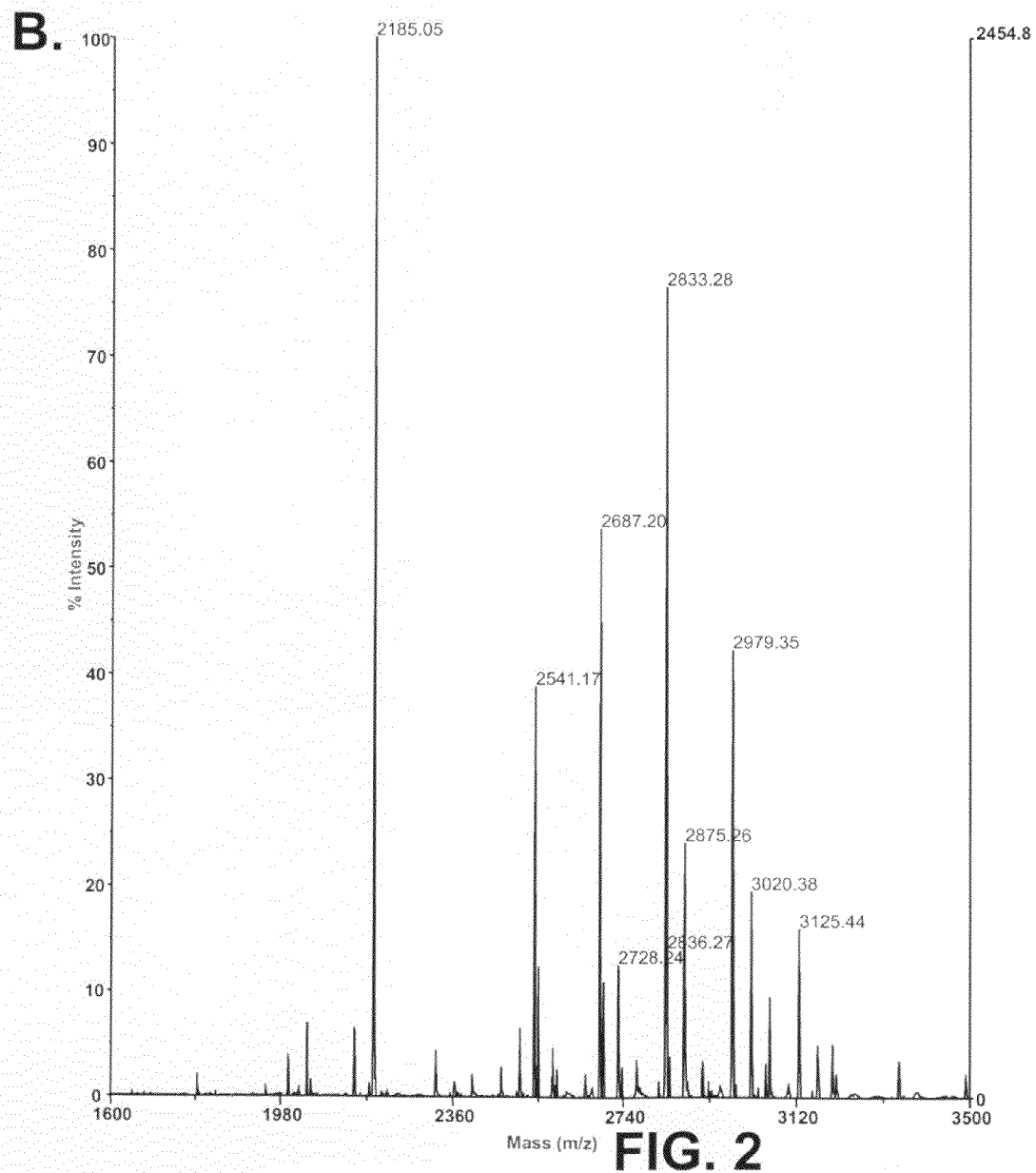

FIG. 2 shows representative mass profiles of the N-linked glycans on EPO produced in an adherent PER.C6™ cell culture and in a PER.C6™ suspension cell culture in serum-free medium. The mass profiles are clearly different and show that the masses of the N-linked sugars produced in the suspension culture are generally much larger than those produced in the adherent culture, indicating that EPO is more extensively glycosylated in PER.C6™ cells that have been cultured in suspension in serum-free medium.

To obtain more insight in the differences in glycosylation under the different cell culture conditions, glycan compositions and carbohydrate structures were assigned to the peaks observed in the mass spectra using the GlycoMod software (www.expasy.ch/tools/glycomod). This software basically predicts the number of N-acetyl-hexosamines (HexNAc), Hexoses (Hex), and deoxyhexoses (dHex) that are part of a glycan structure with any particular observed mass. Using this method, complex type carbohydrate compositions could be accurately assigned to all peaks with an intensity of ≧10%. There were no indications that any of the peaks with an intensity of ≧10% contained phosphate or sulphate. To further predict the structure of the carbohydrates, it was assumed that the N-linked sugars all contained a basic core structure of two HexNAcs (2×GlcNAc), three hexoses (3×mannose) and one dHex (1×fucose). This assumption was based on the generally known fucosylated core-structure of complex type N-linked sugars (Varki et al., 1999) and on sequence data of the N-glycans on PER.C6™-produced EPO as described in WO 03/038100 (incorporated by reference), which confirmed that essentially all N-linked glycans on PER.C6™-produced EPO contain a fucosylated core structure. The mass profiles of PER.C6™-produced EPO (see, for example, FIG. 2) showed that all sugar species observed have a bigger mass than one that corresponds to a fucosylated core only. The N-glycans of the PER.C6™-produced EPO therefore contain, in addition to this fucosylated core structure, other HexNAc and/or Hex and/or dHex residues. These residues form the antennae of the complex N-linked sugars. It was assumed that any additional dHex residue would be an α-1,3-linked fucose, that any additional Hex residue would be a galactose, and that any additional dHex residue would be either GlcNAc or GalNAc. This assumption was made on the basis of the generally known structures of complex type N-linked sugars made by mammalian and human cells (Varki et al., 1999), on the sequence data of the N-glycans on PER.C6™-produced EPO as described in WO 03/038100 (incorporated by reference), and on the observation that the N-linked sugars of PER.C6™-produced EPO can contain GalNAc (also described in WO 03/038100, incorporated by reference).

Based on the above-described assumptions, putative glycan structures were assigned to all peaks with ≧10% intensity present in the mass spectra. The relative peak heights were subsequently used to determine the relative occurrence of the different glycan species. Because the number of Gal residues, which are involved in GlcNAc-Gal (LacNAc) structures, can be deduced from the putative glycan structures, it was possible to calculate the average number of Gal residues per N-linked glycan (EPO contains three N-linked glycans, and, hence, the number obtained can be multiplied by three to obtain the average number of such residues per EPO molecule) present on PER.C6™-EPO (see, Table 1). Table 1 shows that the average number of Gal residues was significantly higher in EPO that was produced in cells that had been adapted for growth in suspension in serum-free medium (VPRO(S)) than in cells that had been grown adherently in the presence of serum (DMEM). It can, therefore, be concluded that the level of galactosylation is significantly increased by adaptation and growth of the cells in suspension and in serum-free medium. Table 1 shows that the average number of GalNAc residues, which are involved in GlcNAc-GalNAc (LacdiNAc) structures, was not much affected by changing the culture conditions. Yet, the average number of putative α-1,3-linked fucose, which forms the so-called Lewis x structure, was significantly increased in cells that had been adapted and cultured in suspension and in serum-free medium. This could be explained, in part, by the fact that galactosylation is increased under these conditions, which, in turn, results in the formation of more GlcNAc-Gal sequences to which an α-1,3-linked fucose can be added. Another structure to which an α-1,3-linked fucose can be added is GlcNAc-GalNAc (LacdiNAc). However, the increased α-1,3-fucosylation does not seem to be due to an increased occurrence of LacdiNAc structures because the average number of GalNAc residues was not much affected by changing the culture conditions.

The average number of Gal+GalNAc residues corresponds to the average number of LacNAc and LacdiNAc structures to which an α-1,3-linked fucose can potentially be added. When the ratio between the occurrence of Gal+GalNAc (part of LacNAc and LacdiNAc structures) and the occurrence of Lewis x structures is determined (see, Table 1), it can be concluded that more than twice as much of the available Gal+GalNAc residues is involved in a Lewis x structure when the cells are grown in suspension in a serum-free medium than when the cells were cultured adherently in the presence of serum. This indicates that the (α-1,3)fucosylation is increased in cells that are cultured in suspension in serum-free medium.

Example 3

Level of Sialylation is Further Increased in Cells that Over-Express α-2,6-sialyltransferase and that are Cultured in Suspension in a Serum-Free Medium We reasoned that the increased level of galactosylation in suspension cultures in serum-free medium would be beneficial in obtaining a higher level of sialylation in cells that over-express the α-2,6-sialyltransferase because the increased galactosylation results in the formation of more GlcNAc-Gal structures to which a sialic acid can be linked. Therefore, PER.C6™-EPO clone 25-3.10 was adapted to suspension culture in serum-free medium and EPO was produced in VPRO medium as described in Example 2.

Figure 3:
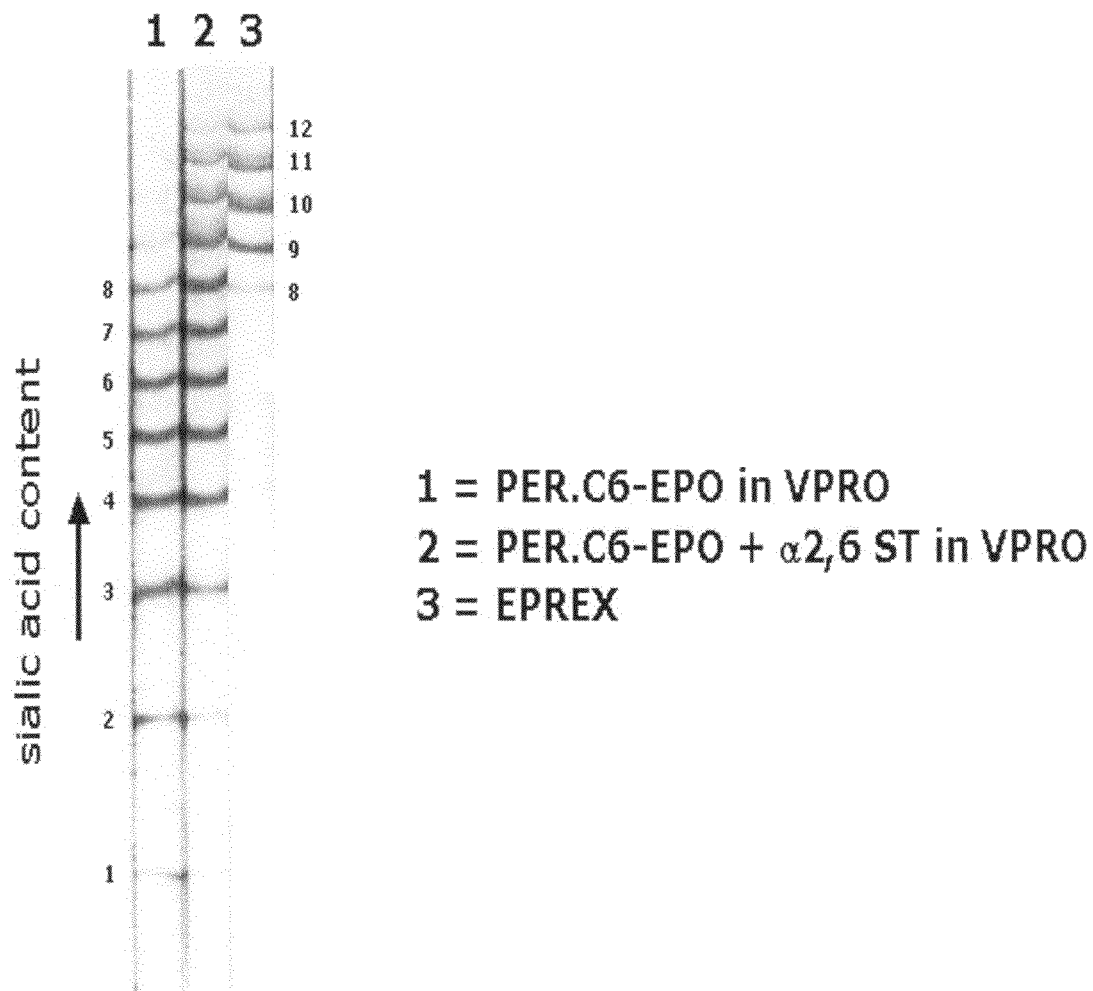
FIG. 3: Sialic acid content as determined by isoelectric focusing of EPO produced in PER.C6™ cells that do not over-express sialyltransferase in a serum-free suspension culture in VPRO medium (lane 1), of EPO produced in PER.C6™ cells that over-express α-2,6-sialyltransferase (i.e., PER.C6™-EPO-ST clone 25-3.10) in a serum-free suspension culture in VPRO (lane 2) and of commercially available EPO, i.e., EPREX™ (lane 3).

The sialic acid content of EPO was analyzed using isoelectric focusing, which was performed essentially as described in WO 03/038100. Instead of visualizing EPO using Western blot analysis, EPO was stained with colloidal blue (Novex). The bands represent EPO isoforms containing different amounts of sialic acids per EPO molecule. The sialic acid content of EPO produced in PER.C6™ cells that over-expressed the α-2,6-sialyltransferase was compared to that of EPREX™ and to EPO produced by PER.C6™ cells that do not over-express the sialyltransferase (FIG. 3). The results demonstrate that EPO produced in PER.C6™ cells over-expressing the rat α-2,6-sialyltransferase contained significantly more sialic acids than EPO produced in PER.C6™ that do not over-express the sialyltransferase. In particular, the highly sialylated EPO isoforms that are present in EPREX™ are well represented in the EPO preparation derived from PER.C6™ cells over-expressing the sialyltransferase, whereas these isoforms are under-represented or absent in the EPO produced in ordinary PER.C6™ cells (i.e., without over-expression of the sialyltransferase). It also appeared that the sialic acid content of EPO derived from PER.C6™-EPO-ST clone 25-3.10 produced in VPRO (in the cells that have been adapted to growth in suspension in serum-free medium) has a higher sialic acid content than EPO derived from the same cell line but not adapted to serum-free medium (compare FIG. 1 with FIG. 3). This indicates that both the adaptation to growth in suspension in serum-free medium and the over-expression of the α-2,6-sialyltransferase contribute to the increased level of sialylation.

Example 4

The Over-Expression of α-2,6-sialyltransferase in PER.C6™ Cells Results in a Reduction of α-1,3 Fucosylation EPO was produced in a serum-free suspension culture of α-2,6-sialyltransferase over-expressing cells, i.e., PER.C6™-EPO-ST 25-3.10 cells and in its parental cell line not over-expressing the sialyltransferase, i.e., PER.C6™-EPO clone 25, to analyze the effects of the over-expression of the α-2,6-sialyltransferase on the glycosylation of EPO. The procedures for production and analysis of the N-linked glycans were as described in Example 2.

The glycan analysis (Table 2) showed that EPO produced by the α-2,6-sialyltransferase over-expressing cells on average contained 0.4-0.6 Lewis x structure per N-linked glycan, whereas the EPO produced by the parental cell line, in which the sialyltransferase was not over-expressed contained 0.9 Lewis x structure per N-linked glycan. This shows that the over-expression of the sialyltransferase caused a reduction of the α-1,3 fucosylation. This suggests that the fucosyltransferases responsible for the addition of α-1,3-linked fucoses compete with the sialyltransferase(s) to modify the terminal GlcNAc-Gal and GlcNAc-GalNAc sequences.

Example 5

Over-Expression of α-2,6-sialyltransferase Results in a High Sialic Acid Content Per N-Linked Glycan In order to determine the effect of the over-expression of the α-2,6-sialyltransferase on the sialylation of the individual N-linked sugars of the PER.C6™-produced EPO (PER.C6™-EPO), the sialic acid content of the N-linked sugars of PER.C6™-EPO was monitored. Therefore, the N-linked sugars of PER.C6™-EPO were separated on charge in order to distinguish between sugars containing 0, 1, 2, 3, or 4 sialic acids.

To do so, PER.C6™-EPO samples derived from cells that do or do not over-express the α-2,6-sialyltransferase were concentrated and buffer-exchanged to 20 mM sodium phosphate (pH 7.2) using Millipore Microcon 10 concentrators to a concentration of approx. 0.25-0.5 Subsequently, the glycoprotein was digested with PNGase F, which releases the N-linked glycans. The released glycans were separated from the protein by ethanol precipitation (75% v/v at 4° C.) and were dried in a Speed Vac centrifuge at room temperature.

Next, the glycans were dissolved and labeled with anthranilic acid (AA) in 10 µl AA in dimethylsulphoxide-glacial acetic acid (30% v/v) containing 1 M cyanoborohydride. The reaction was carried out at 65° C. for two hours, after which the labeling mixture was applied on a cellulose disk (1-cm diameter) in a glass holder. The disk was washed five times with 1 ml 96% (v/v) acetonitrile to remove AA and other reactants. Labeled glycans were eluted with three water washes (0.5 ml) and dried in a Speed Vac centrifuge at room temperature prior to analysis.

The AA-labeled glycans were separated on an HPLC using a weak anion exchange column (Vydac, 301 VHP575P) with a binary gradient of A (20% Acetonitrile in water) and B (500 mM Ammonium Acetate pH 5.0, 20% Acetonitrile) at a flow rate of 0.4 ml/minute. Using this method, the non-, mono-, bi-, tri- and tetra-sialylated glycans were separated, which have been confirmed with known oligosaccharide standards such as NA2, A1, A2[F], A3 and A4F (Glyko Inc., Oxford GlycoSciences, and Dextra-Labs).

Figure 4:
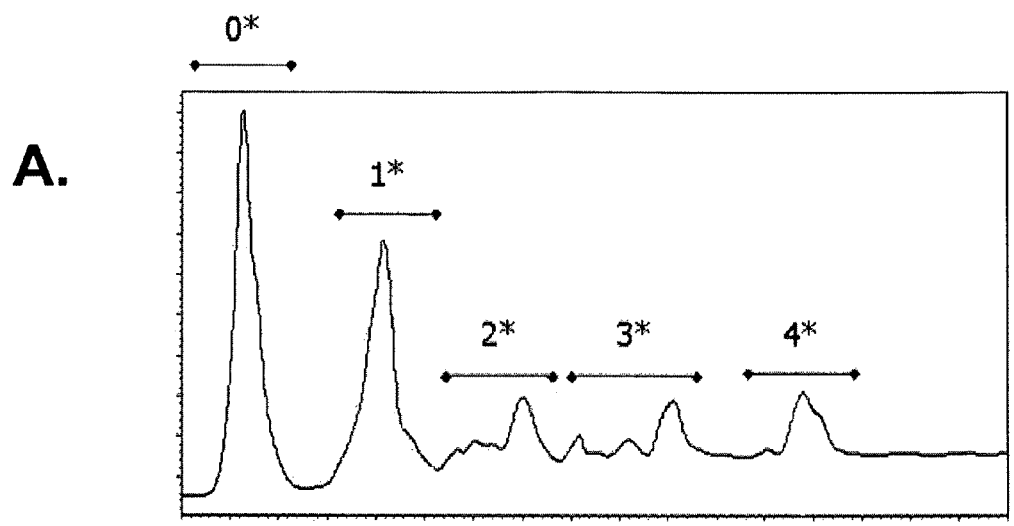
FIG. 4: The number of sialic acids per N-linked sugar of EPO produced by PER.C6™ cells that do not over-express α-2,6-sialyltransferase (PER.C6™-EPO, panel A), and of EPO produced by PER.C6™ cells that do over-express α-2,6-sialyltransferase (PER.C6™-ST-EPO, panel B) was analyzed by HPLC ion-exchange as described in Example 5. The positions where sugars with 0, 1, 2, 3 or 4 sialic acids have been eluted are marked.
Figure 4:
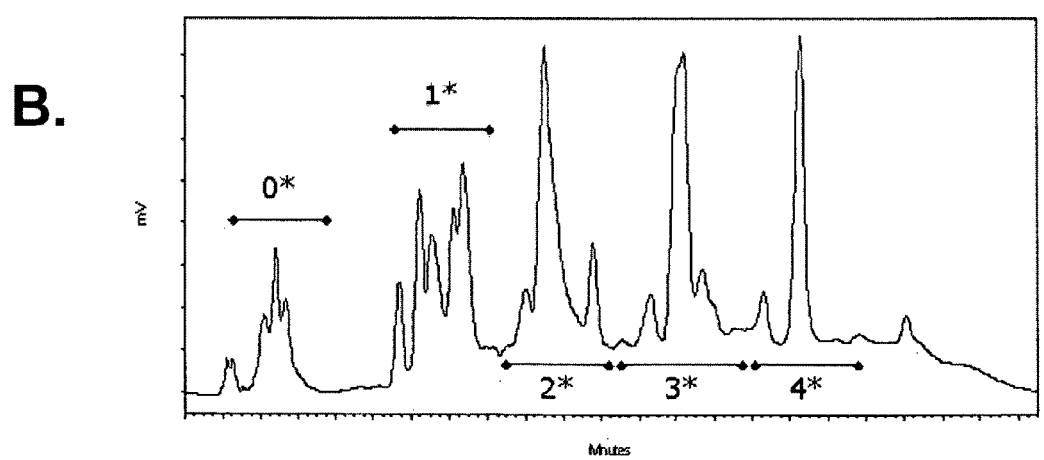

The results in FIG. 4 show that the N-linked sugars of EPO produced in α-2,6-sialyltransferase over-expressing PER.C6™ cells contained significantly more sialic acids that the N-linked sugars of EPO produced in PER.C6™ cells that do not over-express the α-2,6-sialyltransferase. This demonstrates that the over-expression of the α-2,6-sialyltransferase results in the production of N-linked sugars with a greater sialic acid content than when the α-2,6-sialyltransferase is not over-expressed.

Example 6

Isolation of Highly Sialylated PER.C6™-EPO by Ion-Exchange Chromatography

The isolation of highly sialylated EPO produced by PER.C6™ is based on ion-exchange (in particular, anion exchange) chromatography during which the highly sialylated EPO molecules are separated from the less sialylated molecules. First, EPO produced by PER.C6™-EPO-ST Clone 25-3.10 cells according to the methods described in Example 3 was purified by affinity chromatography using the EPO-specific E14 monoclonal antibody as described in WO 03/038100. In this step, EPO was eluted with 0.1 M glycine-HCl, pH 2.7, which was immediately neutralized by adding potassium phosphate buffer, pH 8.0. The resulting buffer was thereafter exchanged using a Hiprep 26/10 desalting column to 20 mM Tris, 20 µM CuSO$_4$ (pH 7). Then, the purified EPO was loaded on a HiTrap Q HP column (Pharmacia). The column was first washed with loading buffer (20 mM Tris, 20 µM CuSO$_4$ (pH 7) and then step-wise eluted with increasing concentrations of elution buffer (20 mM Tris, 20 µM CuSO$_4$, 1 M NaCl). EPO containing a low or medium sialic acid content was first eluted with 11.5% elution buffer (115 mM NaCl) and the highly sialylated EPO was eluted with 25% elution buffer (250 mM NaCl). The sialic acid content of the resulting fractions of EPO was analyzed using isoelectric focusing as described in Example 3.

Figure 5:
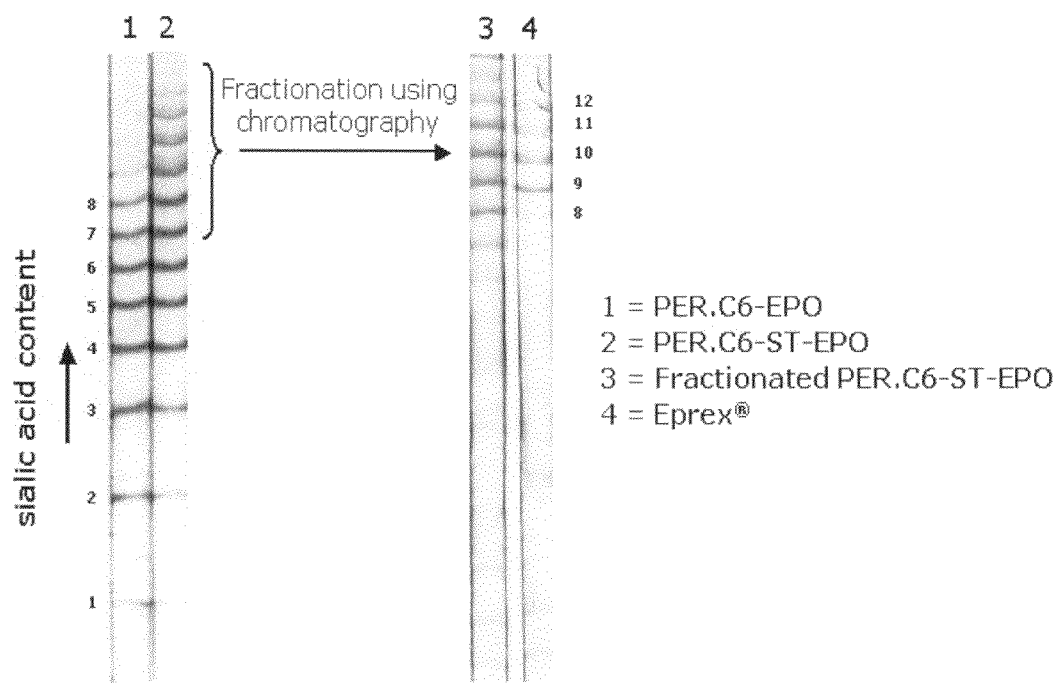
FIG. 5: Isoelectric focusing of various PER.C6™-EPO preparations and EPREX™. PER.C6™-EPO represents the total pool of EPO molecules produced by PER.C6™ cells that do not over-express α-s,6-sialyltransferase; PER.C6™-ST-EPO represents the total pool of EPO molecules produced by PER.C6™ cells that do over-express α-s,6-sialyltransferase. Fractionated PER.C6™-ST-EPO represents the highly sialylated EPO obtained from the material shown in lane 2 using the fractionation/purification protocol that is described in Example 6. EPREX™ represents a commercially available EPO preparation.

FIG. 5 shows the sialic acid content of fractionated and non-fractionated PER.C6™-EPO. The results show that the fractionation procedure resulted in the purification and enrichment of the highly sialylated EPO molecules.

Figure 6:
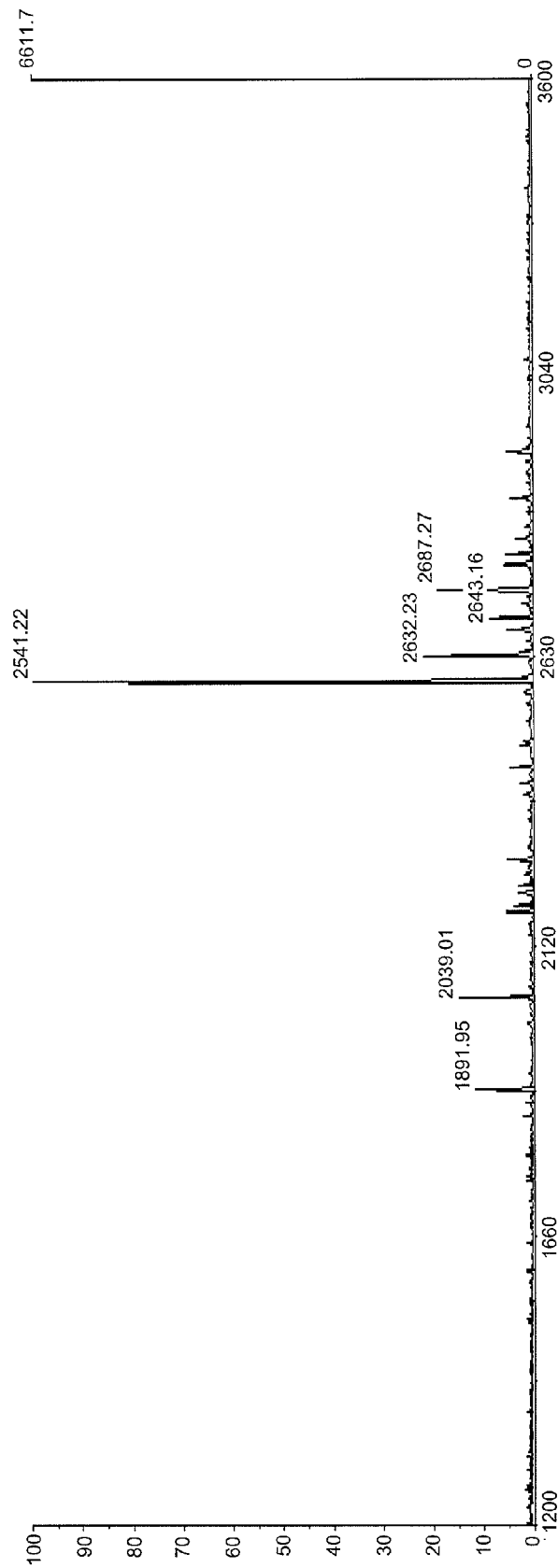
FIG. 6: MALDI-MS spectrum of the desialylated N-linked sugars of fractionated, highly sialylated PER.C6™-EPO as obtained using the procedures described in Example 6.

FIG. 6 shows the MALDI-MS spectrum of the highly sialylated PER.C6™-EPO fraction that was de-sialylated for the mass spectrometry analysis.

The interpretation of the spectrum based on the assumptions described in Example 2 revealed that the fractionated, highly sialylated PER.C6™-EPO preparation contained predominantly tetra-antennary, fully galactosylated N-linked sugars.

The quantification of the average number of Gal, GalNac, and Lewis x structures per N-linked glycan revealed that the fractionated EPO molecules contained a higher average number of Gal residues but a lower average number of GalNAc and Lewis x structures than the total pool of EPO molecules from which they originated (see, Table 3). This shows that EPO molecules with an increased number of Gal residues and a reduced number of GalNAc and Lewis x residues can be selected when highly sialylated EPO molecules are fractionated and enriched on the basis of their charge using ion-exchange chromatography.

Example 7

Erythropoietic Activity of Highly Sialylated PER.C6™-EPO

To show that the increase in sialic acid content of PER.C6™-EPO results in an increased erythropoietic activity, the erythropoietic activity of the highly sialylated PER.C6™-EPO, such as produced according to Example 4, is studied in rats. The potential of recombinant human EPO to stimulate the production of red blood cells can be monitored in a rodent model that has been described by Barbone et al. (1994). According to this model, the increase in the reticulocyte counts is used as a measure for the biological activity of the recombinant human EPO preparation. Reticulocytes are the precursors of red blood cells and their production, in response to EPO, can be used as a measure for the potential of EPO in stimulating the production of red blood cells. An increased production of red blood cells, in turn, leads to a higher hematocrit value.

The activities of the highly sialylated PER.C6™-EPO and EPREX™ are compared in six groups of three Wag/Rij rats. Various doses of PER.C6™-EPO, EPREX™ and diluent buffer as a negative control are injected intravenously in the penile vein at days 0, 1, and 2. PER.C6™-EPO and EPREX™ are administered at a dose of 1, 5, 25, or 125 eU (Elisa units) as determined by the commercially available EPO-specific R&D Elisa Kit. All EPO preparations are diluted to the proper concentration in PBS/0.05% TWEEN® 80 in a total volume of 500 µl. At day 3, 250 µl of EDTA blood is sampled by tongue puncture. On the same day, the percentage of reticulocytes in the total red blood cell population is determined.

Alternatively, the erythropoietic activity is measured in the in vivo bioassay in Normocythaemic mouse according to European Pharmacopoeia (PHEUR 01/2002:1316) (see, Example 13).

Example 8

Figure 7:
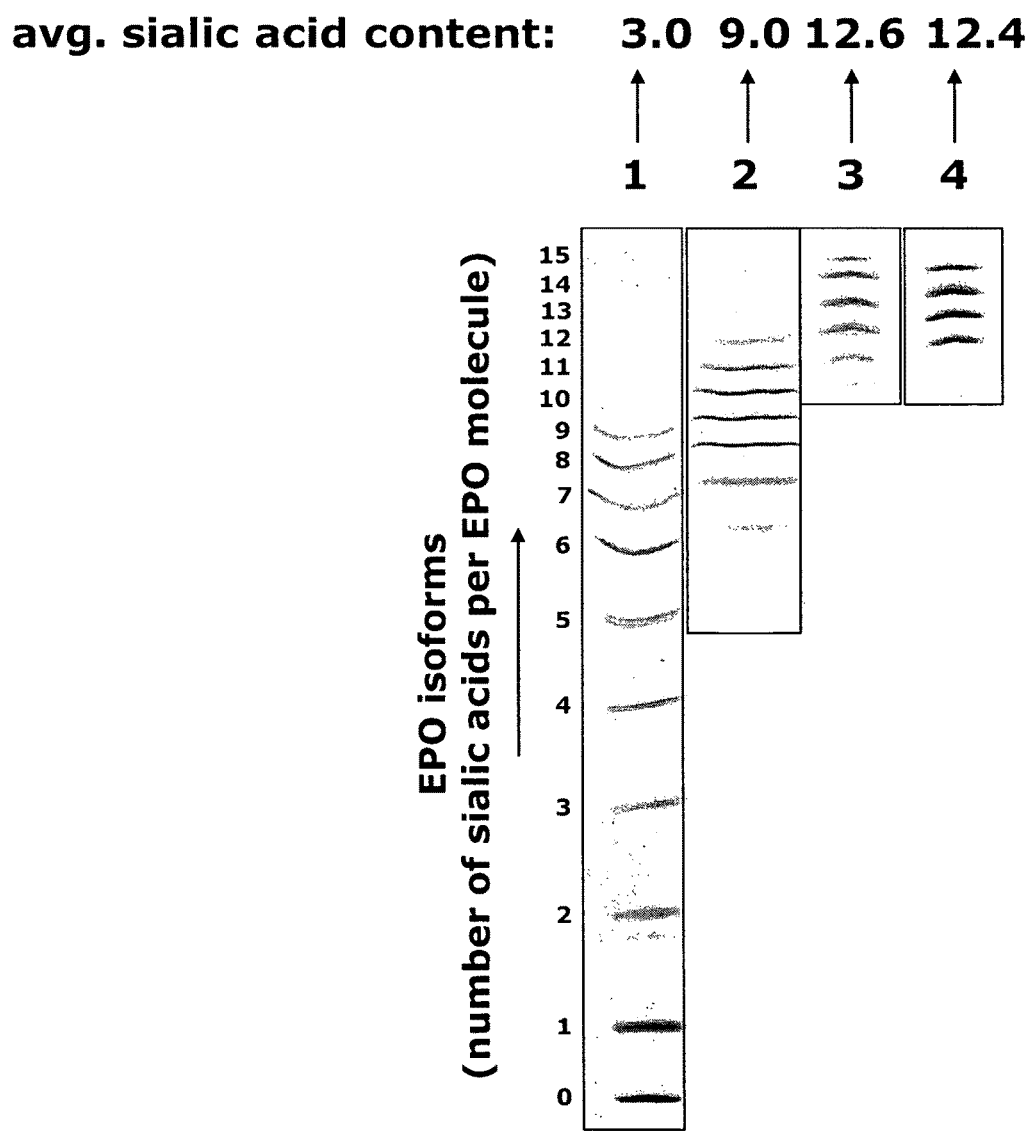
FIG. 7: EPO isoforms with different sialic acid contents as described in this application. 1: EPO produced by PER.C6™ without over-expression of sialyltransferase (Example 2). 2: EPO produced by PER.C6™ with over-expression of α-2,6-sialyltransferase (Example 3). 3: Fractionated highly sialylated EPO (Example 6). 4: EPREX™ (commercially available EPO). See Example 8.

Determination of Sialic Acid Content of PER.C6™-Produced EPO by Isoelectric Focusing and Densitometric Analysis The sialic acid content of various samples of affinity-purified, PER.C6™-produced EPO was analyzed using isoelectric focusing, which was performed on an IsoGel agarose IEF plate (Cambrex) soaked in an ampholyte solution pH 3-10 containing 8 M urea. The EPO bands were visualized with colloidal blue (Novex). As indicated in FIG. 7, the bands represent EPO isoforms containing different numbers of sialic acids per EPO molecule. The relative amount for each isoform was determined using densitometric analysis of the bands. The average number of sialic acid residues per EPO molecule was calculated using the formula:

$$\Sigma(A_n * n)_{n=0-15}$$

A=relative amount of each isoform
n=isoform number (corresponding to the number of sialic acid residues per EPO molecule)

Using this method, the average sialic acid content of EPO produced by the clone PER.C6™-EPO-022 (as described in Example 2), and of EPO produced by the PER.C6™-EPO-ST cell line clone 25-3.10 (as described in Example 3), and of EPO that was obtained after fractionation of the highly sialylated PER.C6™-EPO-ST molecules (as described in Example 6) as well as of EPREX™ was found to be 3.0, 9.0, 12.6 and 12.4, respectively. Alternative methods to calculate the sialic acid content of the recombinant EPO fractions could also be used, e.g., the method described in U.S. Pat. No. 5,856,298, Example 2, or a procedure described in Example 5 of CA 2309810 A1, or a procedure as described by Jourdian et al., J. Biol. Chem. 246, 430 (1971), or modifications of such methods known to the person skilled in the art.

Example 9

Construction of the EPO-ST3 Expression Vector

Figure 8:
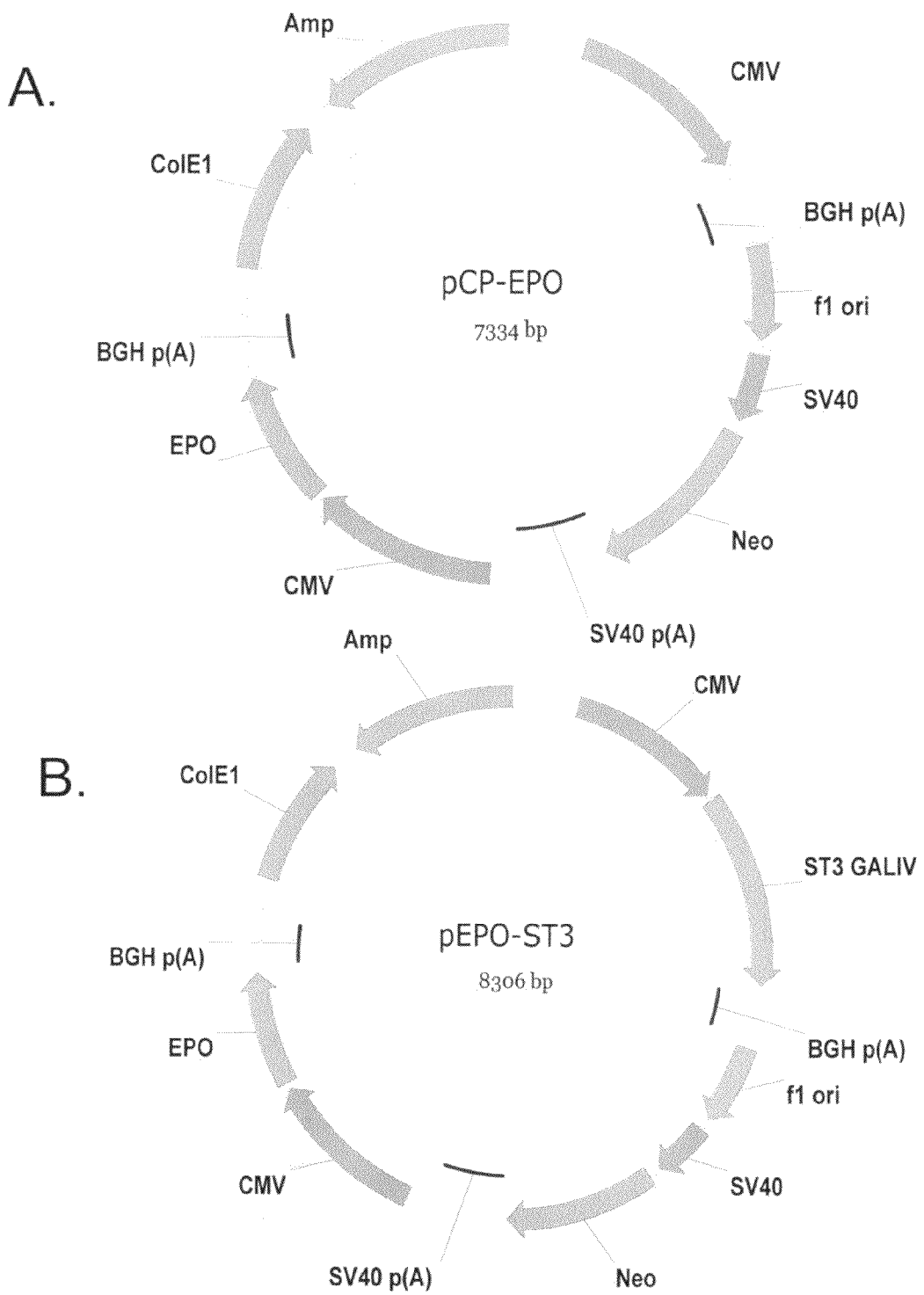
FIG. 8 A-B: Plasmid map of the pCP-EPO and pEPO-ST3 expression vectors. CMV=Cytomegalovirus promoter; BGHp(A)=Bovine Growth Hormone poly-adenylation sequence; f1 ori=f1 origin of replication; SV40=Simian Virus 40 promoter; Neo=Neomycin resistance marker; SV40 p(A) =Simian Virus 40 poly-adenylation sequence; EPO=erythropoietin; ColE1=ColE1 origin of replication; Amp=ampicillin resistance marker. See Example 9.

In order to construct an expression vector for the simultaneous expression of EPO and α-2,3-sialyltransferase, the EPO coding sequence was amplified by PCR (forward primer: 5'-CCAGGCGCGCCACCATGGGGGTGCAC-GAATGTCC-3' (SEQ. ID. NO:1), reverse primer: 5'-CCGGGTTAACTCATCTGTCCCCTGTCCTGC-3' (SEQ. ID. NO:2)). The resulting PCR fragment was digested with AscI and HpaI and inserted into the same restriction sites of expression plasmid pcDNA3002Neo, resulting in the vector pCP-EPO (FIG. 8, Panel A). The human α-2,3-sialyltransferase coding sequence (gene named SIAT4C or STZ; GenBank accession no. L23767, see also U.S. Pat. No. 5,494,790) was amplified by PCR (forward primer: 5'-GGACTAGTG-GATCCGCCACCATG-3' (SEQ. ID. NO:3), reverse primer: 5'-GCTCTAGATCAGAAGGACGTGAGGTTCTTG-3' (SEQ. ID. NO:4)), digested with BamHI and XbaI and inserted into the BamHI and NheI site of pCP-EPO. The resulting vector was named pEPO-ST3 (FIG. 8, Panel B).

Example 10

Transient Expression of pEPO-ST3 in PER.C6™ Cells

Figure 9:
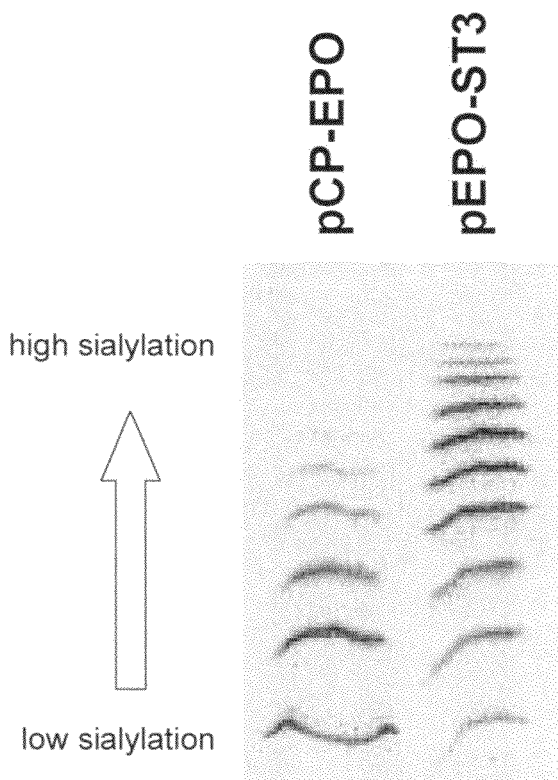
FIG. 9: Isoelectric focusing (IEF) gel of EPO produced in PER.C6™ cells (pCP-EPO) and of EPO produced in PER.C6™ cells under concomitant over-expression of human α-2,3-sialyltransferase (pEPO-ST3), after transient transfection. See Example 10 for details.

The day before transfection, PER.C6™ cells were seeded in T175 culture flasks at a density of 35 million cells/flask and cultured in DMEM, containing 10 mM $MgCl_2$ and 9% fetal bovine serum, at 37° C. and 10% $CO_2$. Transfection was carried out with 28 µg pEPO-ST3 (see, Example 9, FIG. 8, Panel B) or pCP-EPO (as a control; see Example 9, FIG. 8, Panel A) per flask, using Lipofectamine (Gibco) according to the manufacturer's instructions, using techniques well known to persons skilled in the art. Three or four days after transfection, the culture supernatants were harvested and cleared by centrifugation and filtration. The EPO concentrations in the supernatants were determined by ELISA (using a commercially available kit from R&D Systems), and EPO was purified by affinity chromatography. The concentration of the purified EPO samples was determined by HPLC, and 18 µg of the purified EPO samples were subsequently analyzed by isoelectric focusing (IEF) in order to separate the EPO isoforms (FIG. 9). It was found that PER.C6™ cells, transiently transfected with the pEPO-ST3 construct, produced EPO with a significantly increased level of sialylation (as compared to the control construct pCP-EPO, which lacks the α-2,3-sialyltransferase). This demonstrates that, as in an α-2, 6-sialyltransferase, the co-expression of an α-2,3-sialyltransferase can also be used to increase the sialylation level of EPO produced in PER.C6™ cells.

Example 11

Stable Expression of pEPO-ST3 in PER.C6™ Cells

Transfection, Isolation and Screening of Parental Clones
PER.C6™ clones producing highly sialylated erythropoietin (EPO) were generated by expressing human EPO and human α-2,3-sialyltransferase from a single plasmid pEPO-ST3 (see, Example 9). To obtain stable clones, we performed a lipofectamine-based transfection with construct pEPO-ST3. Stable clones were selected in DMEM (Gibco) supplemented with 10% Fetal Bovine Serum containing the selection agent Geneticin® (final concentration 0.5 mg/ml). Three weeks after initiation of the transfection procedure, Geneticin®-resistant clones grew out. A total of 479 clones were selected for isolation. The isolated clones were cultured in selection medium, until 70-90% confluency in 96-well plates. During the passage from 96-well plates to 24-well plates, supernatant were harvested and stored at 2-8° C. until screening. The supernatants of 346 clones were screened for EPO production using an EPO-specific ELISA (QUANTIKINE®IVD®: Human Epo Immunoassay, manufacturer's protocol). Expression levels between clones were found to vary between background levels and more than 400 eU/ml/day. The 15% highest ranked clones and 15% of randomly selected clones (of clones producing more than 50 eU/ml/day but less than the 15% highest producers) were selected for sub-culturing, resulting in a total of 103 clones. During the cell expansion phase, a parallel culture of the selected clones was established for determination of EPO levels. The information from this second screening was used to select 50 clones.

Productivity and Quality of Clones in Serum-Containing Medium
Adherent cultures of these clones were initiated in T80 flasks to generate material for purification/analysis purposes. The cells were cultured in DMEM supplemented with 10% Fetal Bovine Serum for three to five days. Then, the material was harvested. The amount of EPO present in the culture supernatants varies from 541 to 3783 eU/ml.

Figure 10:
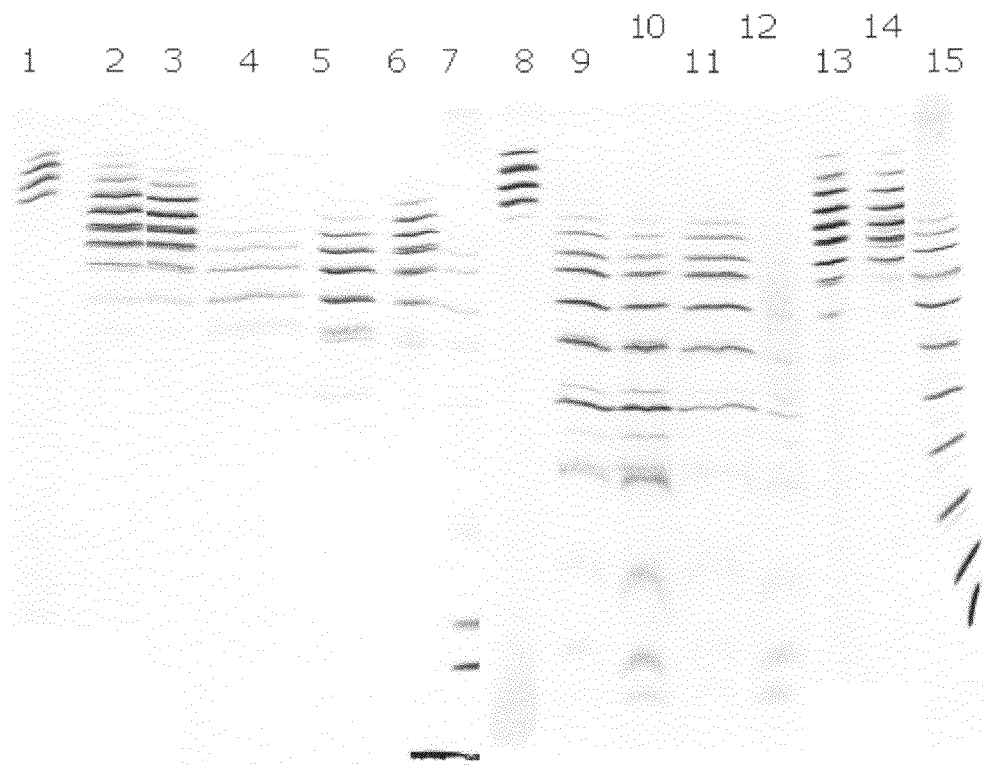
FIG. 10: IEF analysis of stable clones expressing EPO and human α-2,3-sialyltransferase (ST3). Lane 1: EPREX™ (control, commercially available EPO); 2: EPO-ST3 clone 118; 3: EPO-ST3 clone 150; 4: EPO-ST3 clone 165; 5: EPO-ST3 clone 176; 6: EPO-ST3 clone 183; 7: EPO produced in PER.C6™ without over-expressing ST3 (control); 8: EPREX™ (control, commercially available EPO); 9: EPO-ST3 clone 185; 10: EPO-ST3 clone 186; 11: EPO-ST3 clone 199; 12: EPO-ST3 clone 213; 13: EPO-ST3 clone 028; 14: EPO-ST3 clone 059; 15: EPO produced in PER.C6™ without over-expressing ST3 (control). See Example 11 for details.

After purification of EPO by affinity chromatography, the samples were analyzed by Isoelectric Focusing Gel electrophoresis, as described supra. Representative results are presented in FIG. 10. Some clones did not appear to have a strongly increased sialylation level of EPO (e.g., lanes 9-12), but it can be seen that EPO produced by several of the analyzed clones has significantly improved sialylation (i.e., on average more EPO isoforms with high numbers of sialic acids) compared to EPO produced without over-expression of α-2,3-sialyltransferase (e.g., lanes 2, 3 and, in particular, 13 and 14). Clearly, a screening of several clones is sufficient to identify clones with the desired increased level of sialylation.

In conclusion, co-expression of human EPO and human α-2,3-sialyltransferase from a single plasmid results in clones with increased levels of sialylation of the EPO molecules, as compared to clones expressing EPO only.

Example 12

Stable Expression in Serum-Free Medium of EPO in PER.C6™ Cells Over-Expressing Sialyltransferase: Production and Quality 2,6 EPO and 2,3 EPO Production in Stably Transfected PER.C6™ Cells
In this example, EPO was recombinantly produced in stably transfected PER.C6™ cells over-expressing a sialyltransferase (either α-2,6-sialyltransferase or α-2,3-sialyltransferase, see examples above; such cells are referred to as PER.C6™-ST cells) in serum-free suspension cultures. The EPO preparations produced are referred to as 2,6 EPO and 2,3 EPO, respectively, while EPO produced in PER.C6™ cells that do not over-express sialyltransferase is referred to as PER.C6™-EPO.

Pre-culture: Ampoules containing cryopreserved PER.C6™-ST cells producing EPO, were thawed into Erlenmeyer shake flasks containing Mab medium. Shake flask cultures were maintained in a humidified incubator on orbital shake plateaus (37° C., 5% $CO_2$, 100 RPM). Every two to three days, cells were subcultured with a complete medium exchange by centrifugation. The target seeding density of each passage was $0.2$-$0.3 \times 10^6$ viable cells/mL.

Preparation of Inoculum for the Productions in a Batch Process: to Prepare inoculum, the last pre-culture passage was performed in VPRO medium. PER.C6™-ST cells expressing EPO pre-cultured in Mab medium were subcultured by centrifugation, and a complete medium exchange to VPRO medium was performed. The target seeding cell density was $0.4$-$0.6 \times 10^6$ viable cells/mL, and shake flask cultures were maintained in a humidified incubator on orbital shake plateaus (37° C., 5% $CO_2$, 100 RPM). After three to four days of incubation, the cultures were used as inoculum for the batch productions.

Alternatively, the inoculum was prepared in Mab medium. In this case, the cells pre-cultured in Mab medium were subcultured by centrifugation, and seeded at a target cell density of $0.2$-$0.3 \times 10^6$ viable cells/mL in shake flasks or in bioreactors, containing Mab medium. Shake flask cultures were maintained in a humidified incubator on orbital shake plateaus (37° C., 5% $CO_2$, 100 RPM). Bioreactor settings were as follows: temperature was maintained at 37° C., dissolved oxygen concentration ($dO_2$) was controlled at 50% of air saturation by $O_2$ sparging and culture pH at inoculation was controlled below 7.3 by $CO_2$ addition in the headspace. No low limit pH control was operated. After two to three days of incubation, the cultures were used as inoculum for the batch productions.

Production in batch process: Batch cultures in VPRO medium were initiated by diluting the inoculum prepared in VPRO medium into fresh VPRO medium, or by a complete medium exchange to VPRO medium by centrifugation in case the inoculum had been prepared in Mab medium. Batch cultures were started at a target seeding density of $0.2$-$0.4 \times 10^6$ viable cells/mL in shake flasks or bioreactors. Shake flask cultures were maintained in a humidified incubator on orbital shake plateaus (37° C., 5% $CO_2$, 100 RPM). Bioreactor settings were as follows: temperature was maintained at 37° C., dissolved oxygen concentration ($dO_2$) was controlled at 50% of air saturation by $O_2$ sparging and culture pH at inoculation was controlled below 7.3 by $CO_2$ addition in the headspace. No low limit pH control was operated.

Harvest: Cultures of PER.C6™-ST cells expressing EPO were harvested at one day after the maximum viable cell density had been reached; typically between five to nine days after initiation of the batch cultures. EPO concentrations as determined by Elisa ranged approximately from 1000 to 10000 ELISA Units/mL (1 ELISA Unit (eU) corresponds to between about 5-10 ng), dependent on the cell line, the specific clone, and the culture format.

Harvest of material: Cells were removed from the crude batch harvest by means of centrifugation at 300 g for five minutes (Heraeus, Multifuge), followed by clarification over a disposable coarse clarification filter (Millipore, Clarigard Opticap XL, 3 µm) and a disposable fine filter (Sartorius, Sartopore 2, 0.8/0.45 µm).

Purification and anion exchange: EPO was purified from the filtrated batches on a 90 ml CV mouse monoclonal anti-EPO (IgG1) bound to CNBr-activated Sepharose 4B (Amersham Biotech) column with a flow rate of 5 ml/minute. Elution and fractionation by anion exchange was done as described in Example 6. All fractionated and non-fractionated materials were transferred to Standard Storage Buffer (0.03% TWEEN® 80, 0.5% Glycine in PBS pH 7.4) by means of buffer exchange with a size exclusion column (HiPrep 26/10). After buffer exchange, the samples were sterile filtered over a 0.2 µm filter (Pall, Acrodisc PN4908).

Source 15Q fractionation: Purified material was buffer exchanged using a Hiprep 26/10 desalting column (GE Healthcare) to 20 mM Tris/20 µM $CuSO_4$ pH 8.0. After loading, the Source 15Q column (Amersham) was washed with 20 mM Tris/20 µM $CuSO_4$ 50 mM NaCl pH 6.0, followed by elution with increasing amounts of (1 M) NaCl in 20 mM Tris/20 µM CuSO4 pH 6.0. Step gradients of 5-15%, 15-25%, 25-30%, 30-50%, and 50-100% were used. Fractions eluting at 250-300 mM NaCl were pooled. The sialic acid content of the fractions of EPO was analyzed using IEF as described in Example 3. After analysis, fractions were pooled.

The 2,6 EPO thus obtained had an average sialic acid content of 12.1, and the 2,3 EPO thus obtained had an average sialic acid content of 12.7.

Figure 11:
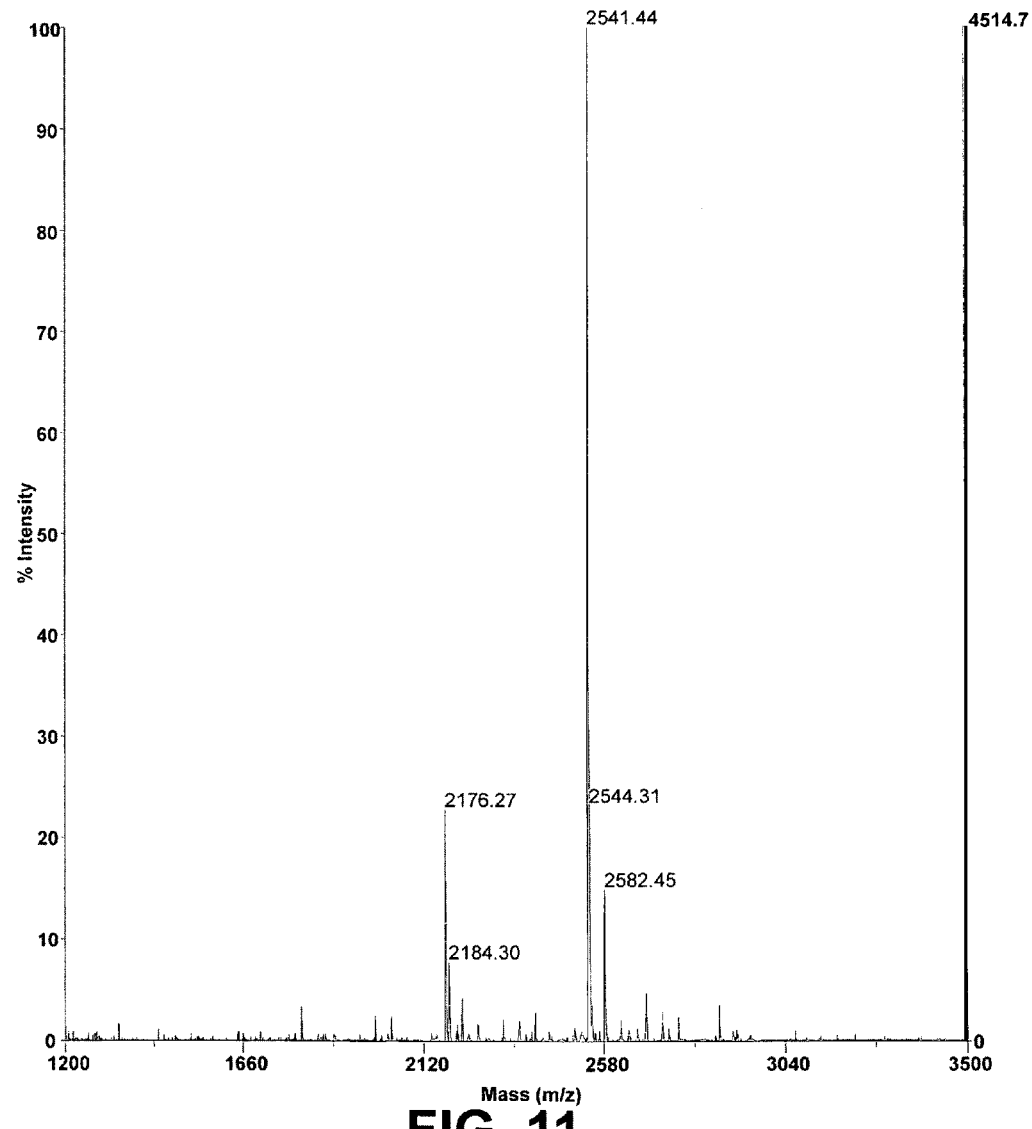
FIG. 11: MALDI-MS spectrum of the desialylated N-linked sugars of affinity-purified 2,3 EPO (see, Example 12 for details).

MALDI analysis: The MALDI spectrum of 2,3 EPO (see, FIG. 11) was made and analyzed according to the methods described in Example 2. Table 5 shows some characteristics of the N-linked sugars of 2,3 EPO and compared to those of PER.C6™-EPO. The analysis of the N-linked sugars revealed that 2,3 EPO contains relatively more of tri- and tetra-antennary sugars as compared to PER.C6™-EPO. This indicates that the over-expression of the α-2,3-sialyltransferase results in a more complete branching of the N-linked sugars. In addition, Lewis x could not be detected in 2,3 EPO which demonstrates that the over-expression of the α-2,3-sialyltransferase resulted in a virtually complete inhibition of α-1,3-fucosylation. Furthermore, whereas PER.C6™-EPO was found to contain a high amount of bi-antennary fucosylated LacdiNAc structures (with an m/z value of 2185.05, see Example 2), these structures were virtually absent in 2,3 EPO. This shows that the over-expression of an α-2,3-sialyltransferase results in the inhibition of the formation of LacdiNAc structures.

Analysis of Fractionated 2,3 EPO and 2,6 EPO

Analysis by SDS-PAGE demonstrated a slightly lower apparent molecular mass as compared to commercially available EPO (EPREX™), which difference disappeared upon removal of the N-linked glycans by PNGaseF. In addition, analysis by size exclusion chromatography (HP-SEC) showed a slightly increased retention time of 2,6 EPO and 2,3 EPO, as compared to EPREX™, which difference disappeared upon removal of N-linked glycans. MALDI spectra were prepared according to the method described in Example 2. No Lewis x-containing peaks were observed with an intensity of ≧10% in 2,3 EPO, in contrast to 2,6 EPO and PER.C6™-EPO. No lactosamine repeat-containing peaks were detected with an intensity of ≧10% in 2,3 EPO and 2,6 EPO.

Example 13

Biological Activity of EPO

PER.C6™-EPO (as produced in PER.C6™ cells not over-expressing a sialyltransferase in serum-free medium, as described in Example 2) and 2,3 EPO and 2,6 EPO (as produced in Example 12) were tested for in vitro and in vivo biological activity. The in vitro biological activity was tested by measuring the capacity to stimulate the proliferation of UT-7 cells in comparison to EPO BRP (EPO reference standard). PER.C6™-EPO, PER.C6™ 2,3 EPO and PER.C6™ 2,6 EPO had a relative potency of 60%, 129% and 94%, respectively, as compared to EPO-BRP suggesting full functionality of the produced EPO in vitro.

The in vivo biological activity of PER.C6™-EPO, PER.C6™ 2,3 EPO and PER.C6™ 2,6 EPO was tested in the in vivo bioassay in the Normocythaemic mouse according to European Pharmacopoeia (PHEUR 01/2002:1316). As shown in Table 6, the in vivo activity of PER.C6™-EPO was below the detection limit, whereas that of 2,6 EPO was 15% and 2,3 EPO was 32% of that of EPO BRP (reference standard). The pharmacokinetics of these preparations were in line with the in vivo activity, in that the curves for 2,3 EPO and 2,6 EPO were in between those of PER.C6™-EPO (lowest curve) and EPO BRP (highest curve), the 2,3 EPO having a longer half-life (and larger area under the curve) than the 2,6 EPO (not shown).

Clearly, the EPO produced in PER.C6™ cells that over-express an α-2,6-sialyltransferase or an α-2,3-sialyltransferase has a strongly increased in vivo biological activity as compared to EPO produced in PER.C6™ cells that do not over-express a sialyltransferase.

Example 14

Obtaining and Testing of EPO with Further Increased Sialic Acid Content

It was shown in Example 13 that the EPO with increased α-2,3-sialylation (2,3 EPO), as obtained, had an improved in vivo biological activity, but still was less active than the standard (EPO BRP), while it has a similar sialic acid content. It was tested whether fractions with still further increased sialic acid content could be obtained from the material produced in PER.C6™-ST cells and, if so, whether such fractions would show further improved in vivo biological activity as compared to the starting material.

A novel batch of 2,3 EPO was produced and affinity purified as described in Example 12. To enrich for fractions with a higher sialic acid content, two alternative preparative isoelectric focusing (IEF) methods were used as described below. Alternatively, preparative size exclusion chromatography (HP-SEC) was used.

Ultrodex Purification

Affinity-purified material was further separated on a preparative IEF gel in a low pH range ((Ultrodex, pH 3-5; Amersham Biosciences) in the presence of 5 M Urea. The sample was separated into isoforms. Isoforms were extracted from the Ultrodex by elution with 0.5 M Tris-HCl pH 8.0. Fractions were pooled and dialyzed against PBS. TWEEN® 80 and Glycine were added to respective final concentrations of 0.03% (v/v) and 0.5% (w/v) and the preparation was sterile filtered (0.22 µm Millex-GV filter, Millipore).

Rotofor Purification

Alternatively, affinity-purified material was further separated by using preparative IEF (Rotofor, Biorad). Two and one-half to 5 mg of purified EPO was loaded in the Rotofor and isoforms were separated in a low pH range, pH 2-4, in 5 M Urea. This resulted in a maximum of ten fractions with different isoforms. Appropriate fractions were pooled. These pooled fractions were dialyzed against PBS. TWEEN® 80 and glycine were added to final concentrations of 0.03% (v/v) and 0.5% (w/v), respectively, and the preparation was sterile filtered (0.22 µm Millex-GV filter, Millipore).

The sialic acid content of various fractions of EPO was analyzed using IEF as described in Example 3 and is shown in the table below.

| Sample | Fractionation method | Average SA |
| --- | --- | --- |
| 2.3 EPO-1 | Ultrodex | 13.6 |
| 2.3 EPO-2 | Ultrodex | 14.3 |
| 2.3 EPO-4 | Rotofor | 12.68 |
| 2.3 EPO-5 | HP-SEC | 12.38 |
| 2.3 EPO-6 | Ultrodex | 13.55 |
| 2.3 EPO-7 | Rotofor | 13.00 |
| 2.3 EPO-8 | Rotofor | 14.16 |
| 2.3 EPO-9 | Rotofor | 12.61 |
| 2.3 EPO-10 | Rotofor | 12.22 |

Samples with average SA (sialic acid) content after preparative IEF or HP-SEC.

Figure 12:
FIG. 12: IEF analysis of EPO preparations. Lane 1: PER.C6™-EPO (average sialic acid content 3.1); Lane 2: EPREX™ (control, commercially available EPO, average sialic acid content 12.4); Lane 3: 2,3 EPO-1 (Ultrodex purified, see Example 14, average sialic acid content 13.6); Lane 3: 2,3 EPO-2 (Ultrodex purified, see Example 14, average sialic acid content 14.3).

Samples 2,3 EPO-1 and 2,3 EPO-2 were run alongside PER.C6™-EPO (average SA 3.1) and EPREX™ (average SA 12.4) on an IEF gel, as shown in FIG. 12.

The in vivo biological activity of EPO thus obtained with a sialic acid content of 14.3 (PER.C6™ 2,3 EPO-2, approximate yield 3%) was tested in the in vivo bioassay in the Normocythaemic mouse according to PHEUR 01/2002:1316. The specific activity of this preparation is 113.881 IU/mg (95% confidence interval 94836-139361 IU/mg), which is comparable to that of a commercially available Epo preparation tested (EPREX™, which, in turn, is comparable to the EPO BRP standard both in activity and in sialic acid content).

These experiments demonstrate that it is possible to obtain EPO with a similar in vivo biological activity as commercial EPO preparations, using E1A-expressing cells and methods according to the invention.

Tables

TABLE 1

Average number of Gal, GalNAc, and Lewis x structures per N-linked glycan present on PER.C6 ™-produced EPO. EPO was produced either in an adherent culture (DMEM) or in a suspension culture in the serum-free VPRO medium (VPRO (S)). The last column represents the ratio of the average number of terminal Gal + GalNac residues over the average number of Lewis x structures.

| PER.C6 ™-EPO produced in | Gal | GalNAc | Lewis x | Gal + GalNAc: Lewis x |
| --- | --- | --- | --- | --- |
| DMEM | 1.8 | 0.5 | 0.6 | 4.0 |
| VPRO (S) | 2.7 | 0.7 | 1.9 | 1.8 |

TABLE 2

Average number of Lewis x structures per N-linked glycan present on EPO produced in PER.C6 ™ cells that do (i.e., PER.C6 ™-EPO-ST clone 25-3.20) or do not (i.e., PER.C6 ™-EPO clone 25) over-express the α-2,6-sialyltransferase.

| α-2,6-sialyltransferase | Lewis x |
| --- | --- |
| without | 0.9 |
| with | 0.4-0.6 |

TABLE 3

Average number of Gal, GalNAc, and Lewis x structures per N-linked glycan found in the total pool of EPO molecules that are produced in a serum-free suspension culture of α-2,6-sialyltransferase over-expressing PER.C6 ™ cells and in the highly sialylated EPO fraction thereof, which was obtained using the procedures described in Example 4.

| EPO preparation | Gal | GalNAc | Lewis x |
| --- | --- | --- | --- |
| Total EPO | 2.5 | 0.5 | 0.5 |
| Fractionated EPO | 3.2 | 0.3 | 0.2 |

TABLE 4

Lewis x and sialic acid content on glycans of different EPO preparations (see, Example 8). Contents are per EPO molecule.

| FIG. 15, lane | EPO preparation | Lewis x | Sialic acid |
| --- | --- | --- | --- |
| 1 | PER.C6 ™ suspension serum-free (Example 2) | 5.7 | 3.0 |
| 2 | PER.C6 ™ + over-expressed α-2,6-sialyltransferase suspension serum-free (Example 3) | 1.2-1.8 | 9.0 |
| 3 | Fractionated highly sialylated EPO (Example 6) | 0.6 | 12.6 |
| 4 | EPREX ™ (commercially available EPO) | 0 | 12.4 |

TABLE 5

Antennarity of the N-linked glycans and average Lewis x content per EPO molecule as calculated from MALDI spectra from affinity-purified PER.C6 ™-EPO and 2,3 EPO, as described in Examples 2 and 12.

| EPO preparation | % Antennarity | | | Lewis x |
|---|---|---|---|---|
| | Bi-antennary | Tri-antennary | Tetra-antennary | |
| PER.C6 ™-EPO | 27 | 0 | 73 | 5.6 |
| 2,3 EPO | 0 | 16 | 84 | 0 |

TABLE 6

In vivo activity in Normocythaemic mice (see, Example 13).

| Preparation | Specific activity (IU/mg) (95% CI) | Relative potency (%) (95% CI) |
|---|---|---|
| EPO-BRP | 130,000 | 100 |
| PER.C6 ™-EPO | <4762 | <4 |
| 2,6-EPO | 18906 (15929-22774) | 15 (12-18) |
| 2,3-EPO | 41687 (32948-56080) | 32 (25-43) |

CI: confidence interval

REFERENCES

Byrd P., K. W. Brown, and P. H. Gallimore 1982. Malignant transformation of human embryo retinoblasts by cloned adenovirus 12 DNA. Nature 298:69-71.

Byrd P. J., R. J. A. Grand, and P. H. Gallimore 1988. Differential transformation of primary human embryo retinal cells by adenovirus E1 regions and combinations of E1A+ras. Oncogene 2:477-484.

Delorme E., T. Lorenzini, J. Giffin, F. Martin, F. Jacobsen, T. Boone, and S. Elliot (1992). Role of glycosylation on the secretion and biological activity of erythropoietin. Biochemistry 31:9871-9876.

Fukuta K., R. Abe, T. Yokomatsu, N. Kono, M. Asanagi, F. Omae, M. T. Minowa, M. Takeuchi, and T. Makino (2000). Remodeling of sugar chain structures of human interferon-γ. Glycobiology 4:412-430.

Gallimore P. H., R. J. A. Grand, and P. J. Byrd (1986). Transformation of human embryo retinoblasts with simian virus 40, adenovirus and ras oncogenes. AntiCancer Res. 6:499-508.

Goldwasser E., J. F. Eliason, and D. Sikkema (1975). An assay for erythropoietin in vitro at the milliunit level. Endocrinology 97:315-23.

Gorman C. M., D. Gies, G. McCray, and M. Huang (1989). The human cytomegalovirus major immediate early promoter can be trans-activated by adenovirus early proteins. Virology 171:377-385.

Grabenhorst E., A. Hoffmann, M. Nimtz, G. Zettlmeissl, and H. S. Conradt (1995). Construction of stable BHK-21 cells co-expressing human secretory glycoproteins and human Gal(β1-4)GlcNAc-R α-2,6-sialyltransferase. Eur. J. Biochem. 232:718-725.

Graham F. L., J. Smiley, W. C. Rusell and R. Nairn (1977). Characteristics of a human cell line transformed by DNA from human adenovirus type 5. J. Virol. 36:59-74.

Grundmann U., C. Nehrlich, T. Rein, and G. Zettlmeissl (1990). Complete cDNA sequence encoding human β-galactoside α-2,6-sialyltransferase. Nucleic Acids Res. 18:667.

Harduin-Lepers A., V. Vallejo-Ruiz, M. A. Krzewinski-Recchi, B. Samyn-Petit, S. Julien, and P. Delannoy (2001). The human sialyltransferase family. Biochimie 83:727-737.

Jenkins N., L. Buckberry, A. Marc, and L. Monaco (1998). Genetic engineering of α-2,6-sialyltransferase in recombinant CHO cells. Biochem. Soc. Trans. 26, S115.

Leist M., et al. (2004). Derivatives of erythropoietin that are tissue protective but not erythropoietic. Science 305:239-242.

Minch S. L., P. T. Kallio, and J. E. Bailey (1995). Tissue plasminogen activator co-expressed in Chinese hamster ovary cells with α-(2,6)-sialyltransferase contains NeuAc α-(2,6)Gal β-(1,4)Glc-N-AcR linkages. Biotechn. Prog. 11:348-351.

Nichols W. W., R. Lardenoie, B. J. Ledwith, K. Brouwer, S. Manam, R. Vogels, D. Kaslow, D. Zuidgeest, A. J. Bett, J. Chen and others (2002). Propagation of adenoviral vectors: use of PER.C6™ cells. In: D. Curiel and J. T. Douglas, editors. Adenoviral vectors for gene therapy. San Diego: Elsevier. pp. 129-167.

Olive D. M., W. Al-Mulla, M. Simsek, S. Zarban, and W. al-Nakib (1990). The human cytomegalovirus immediate early enhancer-promoter is responsive to activation by the adenovirus-5 13S E1A gene. Arch. Virol. 112:67-80.

Prati E. G. P., M. Matasci, T. B. Suter, A. Dinter, A. R. Sburlati, and J. E. Bailey (2000). Engineering of coordinated up- and down-regulation of two glycosyltransferases of the O-glycosylation pathway in Chinese hamster ovary (CHO) cells. Biotech. and Bioeng. 68:239-244.

Schiedner G., S. Hertel and S. Kochanek (2000). Efficient transformation of primary human amniocytes by E1 functions of Ad5: generation of new cell lines for adenoviral vector production. Hum. Gene. Ther. 11:2105-2116.

Takeuchi M., N. Inoue, T. W. Strickland, M. Kubota, M. Wada, R. Shimizu, S. Hoshi, H. Kozutsumi, S. Takasaki, and A. Kobata (1989). Relationship between sugar chain structure and biological activity of recombinant human erythropoietin produced in Chinese hamster ovary cells. Proc. Natl. Acad. Sci. U.S.A. 86:7819-7822.

Varki A., R. Cummings, J. Esko, H. Freeze, G. Hart and J. Marth (1999). Essentials of glycobiology. Cold Spring Harbor Laboratory Press, Cold Spring Harbor, N.Y.

Weikert S., D. Papac, J. Briggs, D. Cowfer, S. Tom, M. Gawlitzek, J. Lofgren, S. Mehta, V. Chisholm, N. Modi, S. Eppler, K. Carroll, S. Chamow, D. Peers, P. Berman, and L. Krummen (1999). Engineering Chinese hamster ovary cells to maximize sialic acid content of recombinant glycoproteins. Nature Biotechnology 17:1116-1121.

Yallop C., J. Crowley, J. Cote, K. Hegmans-Brouwer, F. Lagerwerf, R. Cagne, J.C. Martin, N. Oosterhuis, D. J. Opstelten, and A. Bout (2005a). PER.C6™ cells for the manufacture of biopharmaceutical proteins. In: J. Knablein, editor. Modern Biopharmaceuticals. Weinheim: Wiley-VCH Verlag GmbH & Co. KGaA. pp. 779-807.

Yallop C., M. Raamsman, M. Zuijderwijk, Y. Van Noordenburg, A. Vooys, R. Keehnen, B. van Montfort, M. Jansen, F. Lagerwerf, R. Dijkstra and others (2005b). High level production of recombinant IGG in the human cell line PER.C6™. In: F. Godia and M. Fussenegger, editors. Animal cell technology meets genomics: Springer. pp. 533-536.

Yamaguchi K., K. Akai, G. Kawanishi, M. Ueda, S. Masuda, and R. Sasaki (1991). Effects of site-directed removal of N-glycosylation sites in human erythropoietin on its production and biological properties. J. Biol. Chem. 266: 20434-20439.

Zhang X., S. H. Lok, and O. L. Kom (1998). Stable expression of human α-2,6-sialyltransferase in Chinese hamster ovary cells: functional consequences for human erythropoietin expression and bioactivity. Biochem. Biophys. Acta. 27:441-452.

harvesting the expressed EPO from the eukaryotic cell and/or from the culture medium; and purifying and fractionating the EPO to obtain a composition comprising one or more isoforms of an EPO comprising glycans linked thereto wherein the glycans com-

What is claimed is:

1. A method for obtaining a composition comprising one or more isoforms of an erythropoietin (EPO) comprising glycans linked thereto wherein the glycans comprise, on average, at least six (6) sialic acids per EPO molecule and from zero (0) to two (2) Lewis x structures, the method comprising:

providing a eukaryotic cell comprising a nucleic acid sequence encoding an adenoviral E1A protein in expressible format and a nucleic acid encoding an EPO in expressible format, wherein the eukaryotic cell further contains a nucleic acid sequence encoding a sialyltransferase under control of a heterologous promoter;

culturing the eukaryotic cell in a serum-free culture medium, thus allowing expression of an EPO, the adenoviral E1A protein, and the sialyltransferase in the eukaryotic cell;

prise, on average, at least six (6) sialic acids per EPO molecule and from zero (0) to two (2) Lewis x structures.

2. The method according to claim 1, wherein the eukaryotic cell is derived from a human embryonic retina cell.

3. The method according to claim 1, wherein the glycans comprise on average less than one (1) Lewis x structure and at least ten (10) sialic acids per EPO molecule.

4. The method according to claim 1, wherein the glycans comprise, on average, less than one (1) Lewis x structure and between ten (10) and fifteen (15) sialic acids per EPO molecule.

5. The method according to claim 1, wherein the glycans comprise, on average, less than 0.3 Lewis x structure and between thirteen (13) and fifteen (15) sialic acids per EPO molecule.

6. The method according to claim 5, wherein the composition comprises four (4) or less EPO isoforms together accounting for at least 70% of the EPO present in the composition.

7. The method according to claim 1, wherein the sialyltransferase comprises an alpha-2,6-sialyltransferase.

8. The method according to claim 1, wherein the sialyltransferase comprises an alpha-2,3-sialyltransferase.

9. The method according to claim 1, wherein the wherein the eukaryotic cell is derived from a cell deposited under ECACC no. 96022940.

10. The method according to claim 2, wherein the glycans comprise on average less than one (1) Lewis x structure and at least ten (10) sialic acids per EPO molecule.

11. The method according to claim 2, wherein the glycans comprise, on average, from less than one (1) Lewis x structure to no detectable Lewis x structure, and between ten (10) and fifteen (15) sialic acids per EPO molecule.

12. The method according to claim 2, wherein the glycans comprise, on average, from less than 0.3 Lewis x structure to no detectable Lewis x structure, and between thirteen (13) and fifteen (15) sialic acids per EPO molecule.

13. The method according to claim 12, wherein the composition comprises four (4) or less EPO isoforms together accounting for at least 70% of the EPO present in the composition.

14. The method according to claim 3, wherein the glycans comprise, on average, from less than one (1) Lewis x structure to no detectable Lewis x structure, and between ten (10) and fifteen (15) sialic acids per EPO molecule.

15. The method according to claim 3, wherein the glycans comprise, on average, from less than 0.3 Lewis x structure to no detectable Lewis x structure, and between thirteen (13) and fifteen (15) sialic acids per EPO molecule.

16. The method according to claim 15, wherein the composition comprises four (4) or less EPO isoforms together accounting for at least 70% of the EPO present in the composition.

17. The method according to claim 7, wherein the glycans comprise, on average, from less than one (1) Lewis x structure to no detectable Lewis x structure, and between ten (10) and fifteen (15) sialic acids per EPO molecule.

18. The method according to claim 7, wherein the glycans comprise, on average, less than 0.3 Lewis x structure, preferably no detectable Lewis x structure, and between thirteen (13) and fifteen (15) sialic acids per EPO molecule.

19. The method according to claim 8, wherein the glycans comprise, on average, from less than one (1) Lewis x structure to no detectable Lewis x structure, and between ten (10) and fifteen (15) sialic acids per EPO molecule.

20. The method according to claim 8, wherein the glycans comprise, on average, less than 0.3 Lewis x structure, preferably no detectable Lewis x structure, and between thirteen (13) and fifteen (15) sialic acids per EPO molecule.

* * * * *